US009834585B2

(12) United States Patent
Nunn

(10) Patent No.: US 9,834,585 B2
(45) Date of Patent: Dec. 5, 2017

(54) METHOD OF INHIBITING C5 CLEAVAGE

(71) Applicant: VOLUTION IMMUNO PHARMACEUTICALS SA, Geneva (CH)

(72) Inventor: Miles Andrew Nunn, Reading (GB)

(73) Assignee: Volution Immuni Pharmaceuticals SA, Geneva (CH)

( * ) Notice: Subject to any disclaimer, the term of this patent is extended or adjusted under 35 U.S.C. 154(b) by 0 days.

(21) Appl. No.: 14/624,909

(22) Filed: Feb. 18, 2015

(65) Prior Publication Data

US 2016/0096870 A1 Apr. 7, 2016

Related U.S. Application Data

(60) Division of application No. 12/931,640, filed on Feb. 7, 2011, now Pat. No. 8,993,264, which is a continuation of application No. 10/558,937, filed as application No. PCT/GB2004/002341 on Jun. 2, 2004, now Pat. No. 7,884,188.

(30) Foreign Application Priority Data

Jun. 2, 2003 (GB) .................................. 0312619.0
Nov. 25, 2003 (GB) .................................. 0327386.9

(51) Int. Cl.
*A61K 38/00* (2006.01)
*C07K 14/435* (2006.01)

(52) U.S. Cl.
CPC ........ *C07K 14/43527* (2013.01); *A61K 38/00* (2013.01); *G01N 2333/43556* (2013.01); *G01N 2333/4716* (2013.01); *G01N 2500/00* (2013.01); *G01N 2800/42* (2013.01)

(58) Field of Classification Search
None
See application file for complete search history.

(56) References Cited

U.S. PATENT DOCUMENTS 7,884,066 B2 2/2011 Ting
7,884,069 B2 2/2011 Schaebitz et al.
7,884,188 B2 * 2/2011 Nunn ............... C07K 14/43527 530/300
8,993,264 B2 * 3/2015 Nunn ............... C07K 14/43527 435/252

FOREIGN PATENT DOCUMENTS

WO 93/17099 2/1993

OTHER PUBLICATIONS

Bao et al., Transgenic Expression of a Soluble Complement Inhibitor Protects Against Renal Disease and Promotes Survival in MAU/pr Mice, J. Immunol., 168:3601-3607 (2002).
Bedford et al., Influence of complement depletion on sperm function in the female rabbit, J. Reprod. Fertil., 69:523-528 (1983).
Biesecker et al., Derivation of RNA aptamer inhibitors of human complement C5, Immunopharmacology, 42:219-230 (1999).
Cicchetti et al., Combined Inhibition of Apoptosis and Complement Improves Neural Graft Survival of Embryonic Rat and Porcine Mesencephalon in the Rat Brain, Exp. Neurol., 177:376-384 (2002).
Diamond et al., Human CD59 expressed in transgenic mouse hearts inhibits the activation of complement, 3:305-312 (1995).
Ember et al., Characterization of Complement Anaphylatoxins and Their Biological Responses, In: The Human Complement System in Health and Disease, Volanakis, J.E., Frank, M.M. (Eds.), Marcel Dekker, New York, 241-284 (1998).
Fecke et al., Protection of hDAF-transgenic porcine endothelial cells against activation by human complement: role of the membrane attack complex, Xenotransplantation, 9:97-105 (2002).
Fiorante et al., Low molecular weight dextran sulfate prevents complement activation and delays hyperacute rejection in pig-to-human xenotransplantation models, Xenotransplantation, 8:24-35 (2001).
Fitch et al., Pharmacology and Biological Efficacy of a Recombinant, Humanized, Single-Chain Antibody CS Complement Inhibitor in Patients Undergoing Coronary Artery Bypass Graft Surgery With Cardiopulmonary Bypass, Circulation, 100:2499-2506 (1999).
Frei et al., Generation of a monoclonal antibody to mouse CS application in an ELISA assay for detection of anti-CS antibodies, Molecular Cell. Probes, 1:141-149 (1987).
Giclas, P.C., Classical pathway evaluation and alternative pathway evaluation (sections 13.1. and 13.2), In: Current Protocols in Immunology, Editors: J.E. Coligan, AM. Kruisbeek,D.H. Marguiles, E.M. Shevach and W. Strober, vol. 3 (1994).
Homeister et al., Effects of Complement Activation in the Isolated Heart, Circulation Research, 71:303-319 (1992).
Hebell et al., Suppression of the Immune Response by a Soluble Complement Receptor of B Lymphocytes, 254:102-105 (1991).
Jarvis et al., IgM rheumatoid factor and the inhibition of covalent binding of C4b to IgG in immune complexes, Clin. Exp. Rheumatol., 11:135-141 (1993).
Kohl, Anaphylatoxins and infectious and non-infectious inflammatory diseases, Molecular Immunology, 38:175-187 (2001).
Konttinen et al., Complement in acute and chronic arthritides: assessment of C3c, C9 and protectin (CD59) in synovial membrane, Ann. Rheum. Dis., 55:888-894 (1996).
Kroshus et al., A recombinant soluble chimeric complement inhibitor composed of human CD46 and COSS reduces acute cardiac tissue injury in models of pig-to-human heart transplantation, Transplantation, 69:2282-2289 (2000).
Link et al., Selection of phage-displayed anti-guinea pig CS or CSa antibodies and their application in xenotransplantation, Mol. Immunol., 36:1235-1247 (1999).
Miletic et al., Complement activation in stored platelet concentrates, Transfusion, 33:150-154 (1993).

(Continued)

*Primary Examiner* — Hope Robinson
(74) *Attorney, Agent, or Firm* — McNeill Baur PLLC

(57) ABSTRACT

The invention relates to complement inhibitors that inhibit both the classical and alternative complement pathways. In particular, the invention relates to complement inhibitors derived from the salivary glands of haematophagous arthropods that inhibit both the classical and alternative complement pathways. The invention also relates to the use of the complement inhibitors in the treatment and prevention of diseases.

39 Claims, 16 Drawing Sheets

(56) References Cited

OTHER PUBLICATIONS

Mulligan et al., Endothelial Targeting and Enhanced Antiinflammatory Effects of Complement Inhibitors Possessing Sialyl Lewisx Moieties, J. Immunol., 162:4952-4959 (1999).

Paesen et al., Tick Histamine-Binding Proteins: Isolation, Cloning, and Three-Dimensional Structure, Molecular Cell, 3:661-671 (1999).

Paesen et al., Tick histamine-binding proteins: lipocalins with a second binding cavity, Biochim. Biophys. Acta., 1482:92-101 (2000).

Pratt et al., Effects of Complement Inhibition with Soluble Complement Receptor-1 on Vascular Injury and Inflammation during Renal Allograft Rejection in the Rat, Am. J. Pathol., 149:2055-2066 (1996).

Rehrig et al., Complement Inhibitor, Complement Receptor 1-Related Gene/Protein y-Ig . Attenuates Intestinal Damage After the Onset of Mesenteric Ischemia/Reperfusion Injury in Mice, J. Immunol., 167:5921-5927 (2001).

Ribeiro, Ixodes dammini: Salivary Anti-complement Activity, Exp. Parasitol., 64:347-353 (1987).

Rollins et al., Retroviral Vector Producer Cell Killing in Human Serum Is Mediated by Natural Antibody and Complement: Strategies for Evading the Humeral Immune Response, Hum. Gene Ther., 7:619-626 (1996).

Rollins et al., Anti-CS Single Chain Antibody Therapy Blocks Complement & Leukocyte Activation and Reduces Myocardial Tissue Damage in CPB Patients, Mol. Immunol., 35:397 (1998).

Sahu et al., Complement inhibitors: a resurgent concept in anti-inflammatory therapeutics, Immunopharmacology, 49:133-148 (2000).

Sandoval et al., Distal Recognition Site for Classical Pathway Convertase Located in the C345C/Netrin Module of Complement Component CS, J. Immunol., 165:1066-1073 (2000).

Schiller et al., Expression of a Soluble Complement Inhibitor Protects Transgenic Mice from Antibody-Induced Acute Renal Failure, J. Am. Soc. Nephrol., 12:71-79 (2001).

Smith et al., Membrane-targeted complement inhibitors, Mol. Immunol., 38:249-255 (2001).

Solomon et al., Transmission of antibody-induced arthritis is independent of complement component 4 (C4) and the complement receptors 1 and 2 (CD21/35), Eur. J. Immunol., 32:644-651 (2002).

Tanaka et al., Effect of Anticomplement Agent K76 COOH on Hamster-to-Rat and Guinea Pig-to-Rat Heart Xenotransplantation, Transplantation, 62:681-688 (1996).

Thomas et al., Sulfonated Dextran Inhibits Complement Activation and Complement-Dependent Cytotoxicity in an in vitro Model of Hyperacute Xenograft Rejection, Mol. Immunol., 33:643-648 (1996).

Vakeva et al., Myocardial Infarction and Apoptosis After Myocardial Ischemia and Reperfusion—Role of the Terminal Complement Components and Inhibition by Anti-CS Therapy, Circulation, 97:2259-2267 (1998).

Valenzuela et al., Purification, Cloning, and Expression of a Novel Salivary Anticomplement Protein from the Tick, *Ixodes scapularis*, J. Biol. Chem., 275:18717-18723 (2000).

Wang et al., Anti-CS monoclonal antibody therapy prevents collagen-induced arthritis and ameliorates established disease, Proc. Natl. Acad. Sci. USA, 92:8955-8959 (1995).

Wang et al., Amelioration of lupus-like autoimmune disease in NZ8/WF1 mice after treatment with a blocking monoclonal antibody specific for complement component CS, Proc. Natl. Acad. Sci. USA, 93:8563-8568 (1996).

Ward et al., Use of Animal Models to Define Complement Functions, In: Contemporary Immunology: Therapeutic Interventions in the Complement System, Lambris, J.D., Holers, V.M. (Eds.), Humana Press, Totowa, NJ, 237-253 (2000).

Weisman et al., Soluble Human Complement Receptor Type 1: In vivo Inhibitor of Complement Suppressing Post-Ischemic Myocardial Inflammation and Necrosis, Science, 249:146-151 (1990).

Wyss-Coray et al., Prominent neurodegeneration and increased plaque formation in complement-inhibited Alzheimer's mice, Proc. Natl. Acad. Sci. USA, 99:10837-10842 (2002).

Zhang et al., Targeting of Functional Antibody-Decay-accelerating Factor Fusion Proteins to a Cell Surface, J. Biol. Chem., 276:27290-27295 (2001).

McKenzie et al., Regulation of Complement Activity by Vaccinia Virus Complement-Control Protein, J. of Infectious Diseases, 166:1245-1250 (1992).

Asghar et al., Inhibition of Complement by a Series of Substituted 2-Aryl-1, 3-Indandiones: Interaction with the Fifth Component of Complement, Molecular Immunology, 23:459-465 (1986).

White, Jr. et al., Suppression of mouse complement activity by contaminants of technical grade pentachlorophenol, Agents and Actions, 16:385-392 (1985).

Feuillard et al., Comparative study of in vitro inhibition of activation of the classical and alternative pathways of human complement by the magnesium and sodium salts of the anti-inflammatory peptide N-acetyl-aspartyl-glutamic acid (NAAGA), Agent and Actions, 32:343-346 (1991).

Baranda et al., Purification, N-terminal sequencing and diagnostic value of the major antigens of Ornithodoros erraticus and O. moubata, Veterinary Parasitology, 87:193-206 (2000).

Astigarraga et al., Host immune response evasion strategies in Ornithodoros erraticus and O. moubata and their relationship to the development of an antiargasid vaccine, Parasite Immunology, 19:401-410 (1997).

Keller et al., Cloning of the cDNA and Expression of Moubatin, an Inhibitor of Platelet Aggregation, J. Biological Chemistry, 268:5450-5456 (1993).

Mans et al., Pathogenic mechanisms of sand tampan toxicoses induced by the tick, *Ornithodoros savignyi*, Toxicon, 40:1007-1016 (2002).

Mans et al., Identification of putative proteins involved in granule biogenesis of tick salivary glands, Electrophoresis, 22: 1739-1746 (2001).

Bumpers et al., The Effect of a Novel CS Inhibitor (K-76 COONa) on Tumor Cell Chemotaxis, J. Lab. Clin. Med., vol. 102, No. 3: 421-427 (1983).

Evans et al., In Vitro and In Vivo Inhibition of Complement Activity by a Single-chain Fv Fragment Recognizing human CS, Molecular Immunology, vol. 32, No. 16: 1183-1195 (1995).

Rinder et al., Blockade of C5a and C5b-9 Generation Inhibits Leukocyte and Platelet Activation during Extracorporeal Circulation, J. Clin. Invest., vol. 96: 1564-1572 (1995).

Ember et al., Characterization of Complement Anaphylatoxins and Their Biological Responses, In: The Human Complement System in Health and Disease, Volanakis, J.E., Frank, M.M. (Eds.), Marcel Dekker, New York, 241-284.

Seffernick et al., "Melamine deaminase and atrazine chlorohydrolase: 98 percent identical but functionally different." J Bacteriol, 183(8):2405-10 (2001).

Wells, J.A., "Additivity of mutational effects in proteins," Biochemistry, 29(37):8509-17 (1990).

* cited by examiner

```
ATGCTGGTTTTGGTGACCCTGATTTTCTCCTTTTCTGCGAACATCGCATATGCTGACAGC    60
M  L  V  L  V  T  L  I  F  S  F  S  A  N  I  A  Y  A  D  S      20

GAAAGCGACTGCACTGGAAGCGAACCTGTTGACGCCTTCCAAGCTTTCAGTGAGGGCAAA    120
E  S  D  C  T  G  S  E  P  V  D  A  F  Q  A  F  S  E  G  K      40

GAGGCATATGTCCTGGTGAGGTCCACGGATCCCAAAGCGAGGGACTGCTTGAAAGGAGAA    180
E  A  Y  V  L  V  R  S  T  D  P  K  A  R  D  C  L  K  G  E      60

CCAGCCGGAGAAAAGCAGGACAACACGTTGCCGGTGATGATGACGTTTAAGAATGGCACA    240
P  A  G  E  K  Q  D  N  T  L  P  V  M  M  T  F  K  N  G  T      80

GACTGGGCTTCAACCGATTGGACGTTTACTTTGGACGGCGCAAAGGTAACGGCAACCCTT    300
D  W  A  S  T  D  W  T  F  T  L  D  G  A  K  V  T  A  T  L      100

GGTAACCTAACCCAAAATAGGGAAGTGGTCTACGACTCGCAAAGTCATCACTGCCACGTT    360
G  N  L  T  Q  N  R  E  V  V  Y  D  S  Q  S  H  H  C  H  V      120

GACAAGGTCGAGAAGGAAGTTCCAGATTATGAGATGTGGATGCTCGATGCGGGAGGGCTT    420
D  K  V  E  K  E  V  P  D  Y  E  M  W  M  L  D  A  G  G  L      140

GAAGTGGAAGTCGAGTGCTGCCGTCAAAAGCTTGAAGAGTTGGCGTCTGGCAGGAACCAA    480
E  V  E  V  E  C  C  R  Q  K  L  E  E  L  A  S  G  R  N  Q      160

ATGTATCCCCATCTCAAGGACTGCTAG                                     507
M  Y  P  H  L  K  D  C  *                                       168
```

FIG. 4

SEQUENCE LISTING

```
<160> NUMBER OF SEQ ID NOS: 19

<210> SEQ ID NO 1
<211> LENGTH: 507
<212> TYPE: DNA
<213> ORGANISM: Ornithodoros moubata

<400> SEQUENCE: 1

atgctggttt tggtgaccct gattttctcc ttttctgcga acatcgcata tgctgacagc      60

gaaagcgact gcactggaag cgaacctgtt gacgccttcc aagctttcag tgagggcaaa     120

gaggcatatg tcctggtgag gtccacggat cccaaagcga gggactgctt gaaaggagaa     180

ccagccggag aaaagcagga caacacgttg ccggtgatga tgacgtttaa gaatggcaca     240

gactgggctt caaccgattg gacgtttact ttggacggcg caaaggtaac ggcaaccctt     300

ggtaacctaa cccaaaatag ggaagtggtc tacgactcgc aaagtcatca ctgccacgtt     360

gacaaggtcg agaaggaagt tccagattat gagatgtgga tgctcgatgc gggagggctt     420

gaagtggaag tcgagtgctg ccgtcaaaag cttgaagagt tggcgtctgg caggaaccaa     480

atgtatcccc atctcaagga ctgctag                                         507


<210> SEQ ID NO 2
<211> LENGTH: 168
<212> TYPE: PRT
<213> ORGANISM: Ornithodoros moubata

<400> SEQUENCE: 2

Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160

Met Tyr Pro His Leu Lys Asp Cys
                165
```

-continued

<210> SEQ ID NO 3
<211> LENGTH: 163
<212> TYPE: PRT
<213> ORGANISM: Ornithodoros savignyi

<400> SEQUENCE: 3

```
Met Met Leu Val Leu Ala Thr Val Ile Leu Ser Phe Ser Ala Ser Thr
 1               5                  10                  15

Ala Leu Ala Asp Cys Pro Thr Gly Lys Pro Thr Glu Ala Tyr Val Ala
            20                  25                  30

Phe Asn Glu Gly Lys Gly Ala Tyr Ile Leu Val Arg Ser Thr Asn Leu
        35                  40                  45

Asn Ala Arg Asp Cys Leu Lys Gly Glu Ala Thr Gly Lys Lys Glu Gly
    50                  55                  60

Asn Thr Leu Pro Val Met Met Ala Phe Lys Asp Glu Gly Lys Trp Val
65                  70                  75                  80

Ser Leu Pro Trp Thr Phe Thr Leu Asp Gly Pro Lys Val Thr Ala Thr
                85                  90                  95

His Gly Gln Arg Thr Leu Lys Gly Glu Val Val Tyr Asp Val Pro Ser
            100                 105                 110

His His Cys His Ile Glu Lys Leu Glu Ser Gly Ala Tyr Asp Met Trp
        115                 120                 125

Met Leu Glu Ala Gly Gly Leu Glu Val Asp Ile Glu Cys Cys Asn Lys
    130                 135                 140

Arg Tyr Asp Glu Leu Thr Ser Gly Gln Val Val Ile Arg Pro Gln Asp
145                 150                 155                 160

Lys Asp Cys
```

<210> SEQ ID NO 4
<211> LENGTH: 163
<212> TYPE: PRT
<213> ORGANISM: Ornithodorus savignyi

<400> SEQUENCE: 4

```
Met Met Leu Val Leu Ala Thr Val Ile Leu Ser Phe Ser Ala Ser Thr
 1               5                  10                  15

Ala Leu Ala Asp Cys Pro Thr Gly Lys Pro Thr Asp Ala Tyr Val Ala
            20                  25                  30

Phe Asn Glu Gly Gln Gly Ala Tyr Ile Leu Val Lys Ser Thr Asp Leu
        35                  40                  45

Asp Ala Arg Asp Cys Leu Lys Gly Ser Ala Thr Gly Lys Lys Glu Gly
    50                  55                  60

Asn Lys Val Pro Val Met Met Ala Phe Lys Asn Glu Gly Gln Trp Val
65                  70                  75                  80

Ser Leu Pro Trp Thr Phe Thr Leu Asp Gly Pro Lys Val Thr Ala Thr
                85                  90                  95

Asp Gly Gln Arg Thr Leu Lys Arg Glu Val Val Tyr Asp Val Ala Ser
            100                 105                 110

His His Cys His Val Glu Lys Leu Ala Ser Gly Ala Tyr Glu Met Trp
        115                 120                 125

Met Leu Glu Ala Gly Gly Leu Glu Val Asp Ile Glu Cys Cys Asn Lys
    130                 135                 140

Lys Tyr Asp Glu Leu Thr Ser Gly Gln Val Val Ile Arg Pro Gln Asp
145                 150                 155                 160

Lys Asp Cys
```

<210> SEQ ID NO 5
<211> LENGTH: 171
<212> TYPE: PRT
<213> ORGANISM: Ornithodorus moubata

<400> SEQUENCE: 5

```
Met Met Leu Val Leu Thr Thr Leu Ile Phe Ser Phe Ser Ala Ser Ile
 1               5                  10                  15

Ala Tyr Ala Gln Ser Gly Cys Ser Val Ser Asp Pro Leu Asp Ala Leu
            20                  25                  30

Lys Ala Phe Lys Asp Gly Ala Gly Thr Phe Leu Leu Gln Lys Ser Thr
        35                  40                  45

Asp Pro Gln Ala Arg Asp Cys Leu Lys Gly Thr Pro Asn Gly Asn Arg
    50                  55                  60

Asp Gly Asn Thr Leu Pro Val Thr Met Thr Tyr Lys Asp Asp Ser Lys
65                  70                  75                  80

Trp Val Ser Leu Asn Trp Met Phe Thr Leu Glu Gly Ala Asn Ile Val
                85                  90                  95

Ala Thr Leu Glu Gly Lys Arg Lys Gln Arg Gly Glu Leu Val Tyr Asp
            100                 105                 110

Val Gln Ser His Asp Cys His Ile Thr Lys Leu Ser Ser Gly Val Tyr
        115                 120                 125

Gln Gln Trp Gln Ser Asn Gly Ser Ala Asp Asp Lys Asp Ile Lys Cys
    130                 135                 140

Cys Asp Glu Lys Phe Lys Glu Leu Thr Ser Gly Ile Asp Tyr Thr Lys
145                 150                 155                 160

Pro Gln Glu Lys Gly Cys Glu Thr Ser Ala Lys
                165                 170
```

<210> SEQ ID NO 6
<211> LENGTH: 168
<212> TYPE: PRT
<213> ORGANISM: Ornithodoros moubata

<400> SEQUENCE: 6

```
Met Leu Val Leu Val Thr Leu Ile Phe Ser Phe Ser Ala Asn Ile Ala
 1               5                  10                  15

Tyr Ala Asp Ser Glu Ser Asp Cys Ser Gly Ser Glu Pro Val Asp Ala
            20                  25                  30

Phe Gln Ala Phe Ser Glu Gly Lys Glu Ala Tyr Val Leu Val Arg Ser
        35                  40                  45

Thr Asp Pro Lys Ala Arg Asp Cys Leu Lys Gly Glu Pro Ala Gly Glu
    50                  55                  60

Lys Gln Asp Asn Thr Leu Pro Val Met Met Thr Phe Lys Asn Gly Thr
65                  70                  75                  80

Asp Trp Ala Ser Thr Asp Trp Thr Phe Thr Leu Asp Gly Ala Lys Val
                85                  90                  95

Thr Ala Thr Leu Gly Asn Leu Thr Gln Asn Arg Glu Val Val Tyr Asp
            100                 105                 110

Ser Gln Ser His His Cys His Val Asp Lys Val Glu Lys Glu Val Pro
        115                 120                 125

Asp Tyr Glu Met Trp Met Leu Asp Ala Gly Gly Leu Glu Val Glu Val
    130                 135                 140

Glu Cys Cys Arg Gln Lys Leu Glu Glu Leu Ala Ser Gly Arg Asn Gln
145                 150                 155                 160
```

Met Tyr Pro His Leu Lys Asp Cys
165

<210> SEQ ID NO 7
<211> LENGTH: 163
<212> TYPE: PRT
<213> ORGANISM: Ornithodoros savignyi

<400> SEQUENCE: 7

Met Met Leu Val Leu Ala Thr Val Ile Leu Ser Phe Ser Ala Ser Thr
1 5 10 15

Ala Leu Ala Asp Cys Pro Thr Gly Lys Pro Thr Glu Ala Tyr Val Ala
20 25 30

Phe Asn Glu Gly Lys Gly Ala Tyr Ile Leu Val Arg Ser Thr Asn Leu
35 40 45

Asn Ala Arg Asp Cys Leu Lys Gly Glu Ala Thr Gly Lys Lys Glu Gly
50 55 60

Asn Thr Leu Pro Val Met Met Ala Phe Lys Asp Glu Gly Lys Trp Val
65 70 75 80

Ser Leu Pro Trp Thr Phe Thr Leu Asp Gly Pro Lys Val Thr Ala Thr
85 90 95

His Gly Gln Arg Thr Leu Lys Gly Glu Val Val Tyr Asp Val Pro Ser
100 105 110

His His Cys His Ile Glu Lys Leu Glu Ser Gly Ala Tyr Asp Met Trp
115 120 125

Met Leu Glu Ala Gly Gly Leu Glu Val Asp Ile Glu Cys Cys Asn Lys
130 135 140

Arg Tyr Asp Glu Leu Thr Ser Gly Gln Val Val Ile Arg Pro Gln Asp
145 150 155 160

Lys Asp Cys

<210> SEQ ID NO 8
<211> LENGTH: 163
<212> TYPE: PRT
<213> ORGANISM: Ornithodoros savignyi

<400> SEQUENCE: 8

Met Met Leu Val Leu Ala Thr Val Ile Leu Ser Phe Ser Ala Ser Thr
1 5 10 15

Ala Leu Ala Asp Cys Pro Thr Gly Lys Pro Thr Asp Ala Tyr Val Ala
20 25 30

Phe Asn Glu Gly Gln Gly Ala Tyr Ile Leu Val Lys Ser Thr Asp Leu
35 40 45

Asp Ala Arg Asp Cys Leu Lys Gly Ser Ala Thr Gly Lys Lys Glu Gly
50 55 60

Asn Lys Val Pro Val Met Met Ala Phe Lys Asn Glu Gly Gln Trp Val
65 70 75 80

Ser Leu Pro Trp Thr Phe Thr Leu Asp Gly Pro Lys Val Thr Ala Thr
85 90 95

Asp Gly Gln Arg Thr Leu Lys Arg Glu Val Val Tyr Asp Val Ala Ser
100 105 110

His His Cys His Val Glu Lys Leu Ala Ser Gly Ala Tyr Glu Met Trp
115 120 125

Met Leu Glu Ala Gly Gly Leu Glu Val Asp Ile Glu Cys Cys Asn Lys
130 135 140

Lys Tyr Asp Glu Leu Thr Ser Gly Gln Val Val Ile Arg Pro Gln Asp

```
145                 150                 155                 160

Lys Asp Cys


<210> SEQ ID NO 9
<211> LENGTH: 171
<212> TYPE: PRT
<213> ORGANISM: Ornithodoros moubata

<400> SEQUENCE: 9

Met Met Leu Val Leu Thr Thr Leu Ile Phe Ser Phe Ser Ala Ser Ile
 1               5                  10                  15

Ala Tyr Ala Gln Ser Gly Cys Ser Val Ser Asp Pro Leu Asp Ala Leu
            20                  25                  30

Lys Ala Phe Lys Asp Gly Ala Gly Thr Phe Leu Leu Gln Lys Ser Thr
        35                  40                  45

Asp Pro Gln Ala Arg Asp Cys Leu Lys Gly Thr Pro Asn Gly Asn Arg
    50                  55                  60

Asp Gly Asn Thr Leu Pro Val Thr Met Thr Tyr Lys Asp Asp Ser Lys
65                  70                  75                  80

Trp Val Ser Leu Asn Trp Met Phe Thr Leu Glu Gly Ala Asn Ile Val
                85                  90                  95

Ala Thr Leu Glu Gly Lys Arg Lys Gln Arg Gly Glu Leu Val Tyr Asp
            100                 105                 110

Val Gln Ser His Asp Cys His Ile Thr Lys Leu Ser Ser Gly Val Tyr
        115                 120                 125

Gln Gln Trp Gln Ser Asn Gly Ser Ala Asp Asp Lys Asp Ile Lys Cys
    130                 135                 140

Cys Asp Glu Lys Phe Lys Glu Leu Thr Ser Gly Ile Asp Tyr Thr Lys
145                 150                 155                 160

Pro Gln Glu Lys Gly Cys Glu Thr Ser Ala Lys
                165                 170


<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 10

taatacgact cactatag                                                     18


<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11

aattaaccct cactaaag                                                     18


<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: variant
<222> LOCATION: (5)...(5)
```

<223> OTHER INFORMATION: w is a or t
<220> FEATURE:
<221> NAME/KEY: variant
<222> LOCATION: (6)...(6)
<223> OTHER INFORMATION: s is c or g
<220> FEATURE:
<221> NAME/KEY: variant
<222> LOCATION: (7)...(7)
<223> OTHER INFORMATION: n is a, c, g, or t
<220> FEATURE:
<221> NAME/KEY: variant
<222> LOCATION: (10)...(10)
<223> OTHER INFORMATION: n is a, c, g, or t
<220> FEATURE:
<221> NAME/KEY: variant
<222> LOCATION: (11)...(11)
<223> OTHER INFORMATION: w is a or t
<220> FEATURE:
<221> NAME/KEY: variant
<222> LOCATION: (12)...(12)
<223> OTHER INFORMATION: s is c or g
<220> FEATURE:
<221> NAME/KEY: variant
<222> LOCATION: (13)...(13)
<223> OTHER INFORMATION: n is a, c, g, or t
<220> FEATURE:
<221> NAME/KEY: variant
<222> LOCATION: (16)...(16)
<223> OTHER INFORMATION: r is a or g
<220> FEATURE:
<221> NAME/KEY: variant
<222> LOCATION: (19)...(19)
<223> OTHER INFORMATION: n is a, c, g, or t

<400> SEQUENCE: 12
gtacwsnggn wsngarccng t 21

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
gggaggcttt ctgtatcc 18

<210> SEQ ID NO 14
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 14
cgtccaatcg gttgaag 17

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
gactcgcaaa gtcatcac 18

<210> SEQ ID NO 16
<211> LENGTH: 30
<212> TYPE: DNA
<213> ORGANISM: Artificial Sequence -continued

```
<220> FEATURE:
<223> OTHER INFORMATION: Synthetic Oligonucleotide

<400> SEQUENCE: 16

atagagctca aaatgctggt tttggtgacc                                  30


<210> SEQ ID NO 17
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 17

actgagcggc cgcctagtga tggtgatggt gatgaccgca gtccttgaga tgggg      55


<210> SEQ ID NO 18
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 18

actgagcggc cgcctagcag tccttgagat gggg                             34


<210> SEQ ID NO 19
<211> LENGTH: 17
<212> TYPE: PRT
<213> ORGANISM: Ornithodoros moubata
<220> FEATURE:
<223> OTHER INFORMATION: Synthetic peptide
<220> FEATURE:
<221> NAME/KEY: misc_feature
<222> LOCATION: (6)...(6)
<223> OTHER INFORMATION: Xaa is any amino acid sequence

<400> SEQUENCE: 19

Asp Ser Glu Ser Asp Xaa Ser Gly Ser Glu Pro Val Asp Ala Phe Gln
 1               5                  10                  15

Ala
```

METHOD OF INHIBITING C5 CLEAVAGE

This application is a divisional of U.S. application Ser. No. 12/931,640, filed Feb. 7, 2011, now U.S. Pat. No. 8,993,264, which is a continuation of application Ser. No. 10/558,937, filed Jan. 29, 2017, now U.S. Pat. No. 7,884, 188, which is a national stage application of PCT/GB2004/002341 filed Jun. 2, 2004, which claims priority to United Kingdom Application Serial No. 0327386.9, filed Nov. 25, 2003 and United Kingdom application serial No. 0312619.0, filed Jun. 2, 2003.

The present invention relates to complement inhibitors that inhibit both the classical and alternative complement pathways. In particular, the invention relates to complement inhibitors derived from the salivary glands of haematophagous arthropods that inhibit both the classical and alternative complement pathways. The invention also relates to the use of such complement inhibitors in the treatment and prevention of diseases.

All documents mentioned in the text and listed at the end of this description are incorporated herein by reference.

Complement proteins form the principal arm of the effector immune system (Law and Reid, 1995; Dodds and Sim, 1997; Whaley, 1993). More than 30 proteins in serum and at the cell surface are involved in complement system function and regulation. The system is activated by the presence of foreign antigens. Two activation pathways exist: (1) the classical pathway which is activated by IgM and IgG complexes or by recognition of carbohydrates; and (2) the alternative pathway which is activated by non-self surfaces (lacking specific regulatory molecules) and by bacterial endotoxins. The two pathways comprise parallel cascades of events that result in the production of complement activation through the formation of similar C3 and C5 convertases on cell surfaces resulting in the release of acute mediators of inflammation (C3a and C5a) and formation of the membrane attack complex, as shown in FIG. 1.

The effects of complement activation are wide ranging and include: initiation of inflammation especially through release of the acute mediators C3a and C5a; opsonisation and phagocytosis of pathogens via deposition of C4b and C3b; clearance of immune cell complexes by recruitment of macrophages; increased efficiency of antigen presentation to B cell receptors through covalent association of antigen and C3d; retention of antigen in germinal centres; enhanced antigen uptake by antigen presenting cells; and membrane attack complex (MAC) mediated disruption of foreign or disordered cells (e.g. bacteria, parasites, tumour cells).

Activation of complement must be tightly controlled to prevent damage to the body's own tissues. Control is mediated by the short half-lives of activated proteins, and by control proteins present in plasma and on cell membranes. When complement control goes awry, damage to body tissue may cause disease. Sahu and Lambris (2000) have compiled a list of 29 pathological conditions in which failure to control complement activation has a role.

They include: acute pancreatitis, Alzheimer's disease, allergic encephalomyelitis, allotransplatation, asthma, adult respiratory distress syndrome, burn injuries, Crohn's disease, glomerulonephritis, haemolytic anaemia, haemodialysis, hereditary angioedema, ischaemia reperfusion injuries, multiple system organ failure, multiple sclerosis, myasthenia gravis, myocardial infarction, psoriasis, rheumatoid arthritis, septic shock, systemic lupus erythematosus, stroke, vascular leak syndrome and xenotransplantation. Data derived from animal models (knockout and transgenic mice) demonstrating the essential role of complement activation in some of these diseases has been reviewed by Ward et al., 2000.

Tissue damage arising from complement activation is mediated by the MAC and by the anaphylatoxins, C3a and C5a. These two peptides induce damage through their effects on neutrophils, eosinophils, macrophages, microglial cells, basophils and mast cells. Anaphylatoxin stimulated cells release proinflammatory mediators, tissue degradative enzymes, oxygen free radicals and increase adhesion molecule and inflammatory cytokine expression (Ember et al., 1998). This in turn leads to the elaboration of the immune response and activation of haemostatic mechanisms such as coagulation and fibrinolysis. The role of the anaphylatoxins in infectious and non-infectious inflammatory diseases has recently been reviewed by Kohl (2001). The proinflammatory activity of the MAC is chiefly mediated indirectly by induction of cell activation by causing increased expression of adhesion molecules, tissue factor and chemokines.

In view of the importance of the control of complement in the treatment of medical diseases and disorders, numerous complement inhibitors are under development for therapeutic use (Table 1). None of these inhibitors are yet available in the clinic although some are currently in phase I/II clinical trials. The inhibitory molecules under development are high molecular weight natural inhibitors (Hebell et al., 1991; Weisman et al., 1990) that are often specifically engineered (Mulligan et al., 1999; Smith and Smith, 2001; Zhang et al., 2001). They are generally antibodies directed at specific complement components (Frei et al., 1987; Link et al., 1999), small molecules including RNA aptamers (Biesecker et al., 1999) or molecules that specifically target complement receptors.

TABLE 1

(from Sahu and Lambris, 2000): Complement inhibitors under development

| Inhibitor | Target |
|---|---|
| Protein | |
| C1-Inh | C1 |
| SCR1 | C3b, C4b, C3bBb, $C3b_2Bb$, C4b2a, C4b3b2a |
| Vaccinia CCP | C3b, C4b, C3bBb, $C3b_2Bb$, C4b2a, C4b3b2a |
| SDAF | C3bBb, $C3b_2Bb$, C4b2a, C4b3b2a |
| SMCP | C3b, C4b |
| SMCP-DAF | C3b, C4b, C3bBb, $C3b_2Bb$, C4b2a, C4b3b2a |
| SCD59 | C5b - 8 |
| DAF-CD59 | C3b, C4b, C3bBb, $C3b_2Bb$, C4b2a, C4b3b2a, C5b - 8 |
| C5a mutants | C5aR |
| Anti-C5 antibody | C5 |
| Anti-C3 antibody | C3 |
| Anti-C5a antibody | C5a |
| Anti-C3a antibody | C3a |
| Small molecule | |
| N MeFKPdChaWdR | C5aR |
| F-(OpdChaWR)C5aR | |
| Compstatin | C3 |
| RNA aptamer | C5 |
| BCX-1470 | Factor D |
| FUT-175 | C1s, Factor D, C3bBb, $C3b_2Bb$, C4b2a, C4b3b2a |
| K-76 | C5 |
| Thioester inhibitors | C3, C4 |

In view of the importance of complement inhibitors in the treatment of a wide range of diseases and conditions, there remains a need for additional complement inhibitors.

SUMMARY OF THE INVENTION

According to a first aspect of the invention, there is provided a complement inhibitor molecule that inhibits both the classical and the alternative pathways of complement activation.

By "inhibit" is meant that the effect of the alternative and classical pathways of complement activation is reduced. The ability of a molecule to reduce the effect of the classical complement pathway and the alternative complement pathway can be determined by standard haemolytic assays known in the art, such as those described in the Examples and in Giclas et at (1994). Preferably, the presence of a complement inhibitor molecule of the invention reduces red blood cell lysis in standard haemolytic assays for the classical and alternative pathways of complement activation by at least 20% compared to a standard assay in the absence of a complement inhibitor molecule, more preferably by at least 30%, 40%, 50%, 60%, 70% or 80%.

Preferably, the complement inhibitor molecule of the invention inhibits cleavage of C5 by the C5 convertase in the classical pathway and the C5 convertase in the alternative pathway. As shown in FIG. 1, the conversion of C5 to C5b by C5 convertase occurs in both the alternative complement pathway and the classical complement pathway. The C5 convertase in the classical pathway is C4b3b2a and the C5 convertase in the alternative pathway is $C3b_2Bb$. The inhibition of C5 cleavage by both these C5 convertases thus inhibits both the classical and the alternative pathways of complement activation. The ability of a molecule to inhibit cleavage of C5 by the C5 convertases of the classical and alternative pathways can be determined by standard in vitro assays. Preferably, the presence of a complement inhibitor molecule of the invention reduces cleavage of C5 by the C5 convertases of the classical and alternative pathways by at least 20% compared to a standard assay in the absence of a complement inhibitor molecule, more preferably by at least 30%, 40%, 50%, 60%, 70% or 80%. Preferably, the complement inhibitor molecules of the invention are able to inhibit cleavage of C5 by the C5 convertases of the classical and alternative pathways from a range of mammalian species.

According to a second aspect of the invention, there is provided a complement inhibitor molecule which inhibits cleavage of C5 by a C5 convertase. The complement inhibitor molecule according to this aspect of the invention may inhibit the cleavage of C5 by the C5 convertase of the classical pathway of complement activation. Alternatively, the complement inhibitor molecule of this aspect of the invention may inhibit cleavage of C5 by the C5 convertase of alternative pathway of complement activation. The ability of a molecule to inhibit cleavage of C5 by the C5 convertases of the classical or alternative pathways can be determined by standard in vitro assays as described above. Preferably, the presence of a complement inhibitor molecule of the invention reduces cleavage of C5 by the C5 convertases of the classical or alternative pathways by at least 20% compared to a standard assay in the absence of a complement inhibitor molecule, more preferably by at least 30%, 40%, 50%, 60%, 70% or 80%.

The complement inhibitor molecules of the invention may inhibit cleavage of C5 by the C5 convertases of the classical pathway, the alternative pathway or both the classical and alternative pathways by direct binding to either C5 or to either or both of the C5 convertases. Preferably, the complement inhibitor molecules of the invention inhibit cleavage of C5 by direct binding to C5. Alternatively, the complement inhibitor molecules may inhibit cleavage of C5 by binding to a complex of C5 and a C5 convertase. The invention further provides a complement inhibitor molecule complexed with C5, complexed with a C5 convertase, or complexed with both C5 and a C5 convertase. The C5 convertase in these complexes may be a C5 convertase of either the classical or alternative pathway.

Preferably, the complement inhibitor molecules is derived from a haematophagous arthropod. The term "haematophagous arthropod" includes all arthropods that take a blood meal from a suitable host, such as insects, ticks, lice, fleas and mites.

Complement is one of the first immune defence systems encountered by blood sucking ticks when they attempt to feed. If feeding ticks do not assume rapid control of complement activation, they may be damaged by the host's inflammatory response. An 18.5 kDa protein from the tick *Ixodes scapularis* that inhibits the alternative pathway of complement activation has been cloned and expressed (Valenzuela et al., 2000). Complement inhibitory activity has also been described in *Dermacentor andersoni* (Ribeiro, 1987) and *Ornithodoros moubata* (Astigarraga et al., 1997) salivary gland extract but the active components have not been identified. Molecules that inhibit both the alternative and classical complement pathways have not previously been identified in ticks.

When the complement inhibitor molecule of the invention is derived from a haematophagous arthropod, it is preferably derived from a tick. Preferably, the complement inhibitor molecule is derived from the tick *Ornithodoros moubata*.

Preferably, the complement inhibitor molecule derived from *Ornithdoros moubata* is a protein comprising amino acids 19 to 168 of the amino acid sequence in FIG. 4, or a functional equivalent thereof. In particular, the complement inhibitor molecule is a protein comprising amino acids 1 to 168 of the amino acid sequence in FIG. 4 or a functional equivalent thereof.

The protein having the amino acid sequence given in FIG. 4, also referred to herein as "OmCI protein", was isolated from the salivary glands of the tick *Ornithodoros moubata* and has been found to inhibit the classical and alternative complement pathways. More particularly, it has been found to inhibit cleavage of C5 by the C5 convertases of both the classical and alternative pathways of complement activation, targeting the C5 activation step without affecting C3 activation. The OmCI protein inhibits C5 cleavage by the C5 convertases in a range of mammals. The first 18 amino acids of the OmCI protein sequence given in FIG. 4 form a signal sequence which is not required for complement inhibitory activity. The term "OmCI protein", as used herein, refers to the sequence given in FIG. 4 with or without the signal sequence.

The term "functional equivalent" is used herein to describe homologues and fragments of the OmCI protein which retain the ability to inhibit the classical and the alternative complement pathways. Preferably, functional equivalents retain the ability to inhibit cleavage of C5 by C5 convertases of the classical and alternative pathways. Functional equivalents also include homologues and fragments of the OmCI protein which retain the ability to inhibit the classical pathway by inhibiting cleavage of C5 by the C5 convertase of the classical pathway or which retain the ability to inhibit the alternative pathway of complement by inhibiting cleavage of C5 by the C5 convertase of the alternative pathway.

The term "homologue" is meant to include reference to paralogues and orthologues of the OmCI sequence that is explicitly identified in FIG. 4, including, for example, the OmCI protein sequence from other tick species, including *Rhipicephalus appendiculatus, R. sanguineus, R. bursa, A. americanum, A. cajennense, A. hebraeum, Boophilus microplus, B. annulatus, B. decoloratus, Dermacentor reticulatus, D. andersoni, D. marginatus, D. variabilis, Haemaphysalis inermis, Ha. leachii, Ha. punctata, Hyalomma anatolicum anatolicum, Hy. dromedarii, Hy. marginatum marginatum, Ixodes ricinus, I. persulcatus, I. scapularis, I. hexagonus, Argas persicus, A. reflexus, Ornithodoros erraticus, O. moubata moubata, O. m. porcinus*, and *O. savignyi*. The term "homologue" is also meant to include the OmCI protein sequence from mosquito species, including those of the *Culex, Anopheles* and *Aedes* genera, particularly *Culex quinquefasciatus, Aedes aegypti* and *Anopheles gambiae*; flea species, such as *Ctenocephalides felis* (the cat flea); horseflies; sandflies; blackflies; tsetse flies; lice; mites; leeches; and flatworms.

Methods for the identification of homologues of the OmCI sequence given in FIG. 4 will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database (ncbi.nlm.nih.gov/), the EMBL database (ebi.ac.uk/), the DDBJ database (ddbj.nig.acjp/), the SWISS-PROT protein database (expasy.hcuge.ch/), PIR (pir.georgetown.edu/), TrEMBL (ebi.ac.uk/), the TIGR databases (see tigr.org/tdb/index. html), the NRL-3D database (nbrfa.georgetown.edu), the Protein Data Base (resb.org/pdb), the NRDB database (ncbi.nlm.nih.gov/pub/nrdb/README), the OWL database (biochem.ucl.ac.ukfbsm/dbbrowser/OWL/) and the secondary databases PROSITE (expasy.hcuge.ch/sprot/prosite.html), PRINTS (iupab.leeds.ac.uk/bmb5dp/prints.html), Profiles (ulrec3.unil.ch/software/PFSCAN_form.html), Pfam (sanger.ac.uk/software/pfam), Identify (dna.stanford.edu/identify/) and Blocks (blocks.fucrc.org) databases. Examples of commercially-available databases or private databases include PathoGenome (Genome Therapeutics Inc.) and PathoSeq (Incyte Pharmaceuticals Inc.).

Typically, greater than 30% identity between two polypeptides (preferably, over a specified region) is considered to be an indication of functional equivalence and thus an indication that two proteins are homologous. Preferably, proteins that are homologues have a degree of sequence identity with the OmCI protein sequence identified in FIG. 4 of greater than 60%. More preferred homologues have degrees of identity of greater than 70%, 80%, 90%, 95%, 98% or 99%, respectively with the OmCI protein sequence given in FIG. 4. Percentage identity, as referred to herein, is as determined using BLAST version 2.1.3 using the default parameters specified by the NCBI (the National Center for Biotechnology Information; ncbi.nlm.nih gov/) [Blosum 62 matrix; gap open penalty=11 and gap extension penalty=1].

Homologues of the OmCI protein sequence given in FIG. 4 include mutants containing amino acid substitutions, insertions or deletions from the wild type sequence, provided that inhibition of the classical or alternative complement pathways demonstrated by the wild type protein sequence is retained. Preferably, the mutants retain the ability to inhibit both the classical and alternative complement pathways. Preferably, such mutants retain the ability to inhibit cleavage of C5 by C5 convertases of both the alternative and classical pathways. Mutants that retains the ability to inhibit either the classical or the alternative complement pathway are also included in the term homologue provided that they retain the ability to inhibit cleavage of C5 by either the C5 convertase of the alternative pathway or by the C5 convertase of the classical pathway. Mutants thus include proteins containing conservative amino acid substitutions that do not affect the function or activity of the protein in an adverse manner. This term is also intended to include natural biological variants (e.g. allelic variants or geographical variations within the species from which the OmCI proteins are derived). Mutants with improved activity in the inhibition of the classical or alternative pathways compared to that of the wild type protein sequence may also be designed through the systematic or directed mutation of specific residues in the protein sequence. Preferably, such mutants show improved inhibition of C5 cleavage by the C5 convertase of the classical pathway or by the C5 convertase of the alternative pathways. Preferably, these mutants show improved inhibition of C5 cleavage by C5 convertases of both the alternative and classical pathways.

Fragments of the OmCI protein and of homologues of the OmCI protein are also provided by the invention. Included as such fragments are not only fragments of the *O. moubata* OmCI protein that is explicitly identified herein in FIG. 4, but also fragments of homologues of this protein, as described above. Such fragments of homologues will typically possess greater than 60% identity with fragments of the OmCI protein sequence in FIG. 4, although more preferred fragments of homologues will display degrees of identity of greater than 70%, 80%, 90%, 95%, 98% or 99%, respectively with fragments of the OmCI protein sequence in FIG. 4. Fragments of the OmCI protein comprising the sequence in FIG. 4 and fragments of homologues thereof preferably inhibit the classical and the alternative complement pathways, preferably by inhibiting C5 cleavage by C5 convertases of both the classical and alternative pathways. Fragments of the OmCI protein and of homologues thereof which inhibit either the classical complement pathway or the alternative complement pathway are also included in the invention, provided that they retain the ability to inhibit the cleavage of C5 by either the C5 convertase of the classical pathway or by the C5 convertase of the alternative pathway. Fragments with improved activity in inhibiting the classical or alternative complement pathways and in particular improved activity in inhibiting C5 cleavage by the C5 convertases may, of course, be rationally designed by the systematic mutation or fragmentation of the wild type sequence followed by appropriate activity assays.

The term "functional equivalent" also refers to molecules that are structurally similar to the OmCI protein or that contain similar or identical tertiary structure, particularly in the environment of the active site or active sites of OmCI. OmCI is thought to inhibit cleavage of C5 by the C5 convertases by direct binding to either C5 or to both of the C5 convertases or to complexes of C5 and the C5 convertases. OmCI is shown in the Examples herein to bind to C5, supporting the suggestion that it inhibits cleavage of C5 by the C5 convertases by direct binding to C5 alone or when C5 is part of a complex with a C5 convertase. Although the applicant does not wish to be bound by this theory, it is postulated that binding of OmCI to C5 may prevent access of the C5 convertases to the C5 cleavage site. Preferred functional equivalents of OmCI therefore include molecules, such as homologues and fragments, that retain the ability to bind directly to C5.

OmCI is also believed to be a member of the lipocalin family of proteins that bind small ligands internally. OmCI may therefore also inhibit the cleavage of C5 and or deposition of the MAC indirectly, by binding to a small ligand that would normally bind to C5, C5 convertase or the MAC and that is required for normal function. No small ligands have previously been described as essential for complement system function although the C8 gamma component of the MAC is a lipocalin that may bind a small ligand. Functional equivalents thus include molecules that contain similar or identical tertiary structure to the active site(s) in the OmCI protein that binds to C5 or the C5 convertases and/or the active site in the OmCI protein that binds a small ligand. In particular, synthetic molecules that are designed to mimic the tertiary structure or active site(s) of the OmCI protein are considered to be functional equivalents.

The invention further provides the OmCI protein, or a fragment or a functional equivalent thereof, complexed with C5, complexed with a C5 convertase, or complexed with both C5 and a C5 convertase. The C5 convertase in these complexes may be a C5 convertase of either the classical or alternative pathway.

As discussed in more detail previously, there is a continuing need for complement inhibitors and in particular for complement inhibitors that inhibit both the classical and alternative pathways of complement activation. The complement inhibitor molecules of the invention, including the OmCI protein and functional equivalents thereof, will have a wide range of medical applications, in the treatment, prevention and diagnosis of diseases and conditions, as well as being useful research tools in the study of complement inhibition and of the inhibition of both the alternative and classical pathways of complement activation. The OmCI protein itself will be particularly useful for these applications as it inhibits the complement cascade of diverse mammalian species.

The complement inhibitor molecules of the invention, including the OmCI protein and functional equivalents thereof, may be prepared in recombinant form by expression in a host cell. Such expression methods are well known to those of skill in the art and are described in detail by Sambrook et at (2000) and Fernandez & Hoeffler (1998). The proteins and fragments of the present invention can also be prepared using conventional techniques of protein chemistry. For example, protein fragments may be prepared by chemical synthesis.

According to a further embodiment, the invention provides an antibody which binds to a complement inhibitor molecule as described above. In particular, the invention provides an antibody which binds to the OmCI protein or a functional equivalent thereof. Antisera and monoclonal antibodies can be made by standard protocols using a complement inhibitor molecule, such as the OmCI protein or functional equivalent thereof, as an immunogen (see, for example, Antibodies: A Laboratory Manual ed. By Harlow and Lane, Cold Spring Harbor Press, 1988). As used herein, the term "antibody" includes fragments of antibodies which also bind specifically to a complement inhibitor molecule. The term "antibody" further includes chimeric and humanised antibody molecules having specificity for a complement inhibitor molecule of the invention. In some cases, it will be desirable to attach a label group to the antibody in order to facilitate detection. Preferably, the label is an enzyme, a radiolabel or a fluorescent tag.

Derivatives of the complement inhibitor molecules described above are also included as embodiments of the invention. In particular, the invention provides derivatives of the OmCI protein or of functional equivalents thereof. Such derivatives include a fusion protein comprising a complement inhibitor molecule that is genetically or chemically fused to one or more peptides or polypeptides. The purpose of the additional peptide or polypeptide may be to aid detection, expression, separation or purification of the protein or it may lend the protein additional properties as desired. Examples of potential fusion partners include beta-galactosidase, glutathione-S-transferase, luciferase, a polyhistidine tag, a T7 polymerase fragment and a secretion signal peptide. Other potential fusion partners include potential biopharmaceuticals, such as proteins that are being developed for use as drugs to treat specific diseases.

The complement inhibitor molecule may also be fused to a marker domain. Preferably, the marker domain is a fluorescent tag, an epitope tag that allows purification by affinity binding, an enzyme tag that allows histochemical or fluorescent labelling, or a radiochemical tag. In a preferred embodiment, the marker domain is a radiochemical tag.

Methods for the generation of fusion proteins are standard in the art and will be known to the skilled reader. For example, most general molecular biology, microbiology recombinant DNA technology and immunological techniques can be found in Sambrook et al. (2000) or Ausubel et al. (1991). Generally, fusion proteins may be most conveniently generated recombinantly from nucleic acid molecules in which two nucleic acid sequences are fused together in frame. These fusion proteins will be encoded by nucleic acid molecules that contain the relevant coding sequence of the fusion protein in question.

According to a further aspect of the invention, there is provided a nucleic acid molecule comprising a nucleotide sequence encoding a complement inhibitor molecule according to the above-described aspects of the invention. Such molecules include single- or double-stranded DNA, cDNA and RNA, as well as synthetic nucleic acid species. Preferably, the nucleic acid sequences comprise DNA.

Preferably, the nucleic acid molecule comprises a nucleotide sequence encoding the OmCI protein or a functional equivalent thereof. Preferably, such a nucleic acid molecule comprises bases 53 to 507 of the nucleotide sequence in FIG. 4. This nucleotide sequence encodes the OmCI protein without the signal sequence. The first 54 bases of the nucleotide sequence in FIG. 4 encode the signal sequence of OmCI which is not required for complement inhibitory activity. The invention also provides a nucleic acid molecule comprising bases 1 to 507 of the nucleic acid sequence in FIG. 4 which encodes the OmCI protein with the signal sequence. As used herein, the phrase "nucleic acid molecules encoding the OmCI protein" includes both nucleic acid molecules encoding the OmCI protein with the signal sequence nucleic acid molecules encoding the OmCI protein without the signal sequence.

The invention also includes cloning and expression vectors comprising the nucleic acid molecules of this aspect of the invention. Such expression vectors may incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention.

Additionally, it may be convenient to cause a recombinant protein to be secreted from certain hosts. Accordingly, further components of such vectors may include nucleic acid sequences encoding secretion, signalling and processing sequences.

Vectors according to the invention include plasmids and viruses (including both bacteriophage and eukaryotic viruses), as well as other linear or circular DNA carriers, such as those employing transposable elements or homologous recombination technology. Many such vectors and expression systems are known and documented in the art (Fernandez & Hoeffler, 1998). Particularly suitable viral vectors include baculovirus-, adenovirus- and vaccinia virus-based vectors.

Suitable hosts for recombinant expression include commonly used prokaryotic species, such as *E. coli*, or eukaryotic yeasts that can be made to express high levels of recombinant proteins and that can easily be grown in large quantities. Preferably, the host cell is a eukaryotic yeast cell. Mammalian cell lines grown in vitro are also suitable, particularly when using virus-driven expression systems. Another suitable expression system is the baculovirus expression system that involves the use of insect cells as hosts. An expression system may also constitute host cells that have the DNA incorporated into their genome. Proteins, or protein fragments may also be expressed in vivo, for example in insect larvae or in mammalian tissues.

A variety of techniques may be used to introduce the vectors according to the present invention into prokaryotic or eukaryotic cells. Suitable transformation or transfection techniques are well described in the literature (Sambrook et al, 1989; Ausubel et al, 1991; Spector, Goldman & Leinwald, 1998). In eukaryotic cells, expression systems may either be transient (e.g. episomal) or permanent (chromosomal integration) according to the needs of the system.

The invention also provides antisense nucleic acid molecules which hybridise under high stringency hybridisation conditions to the nucleic acid molecules encoding the complement inhibitor molecules. In particular, the invention provides antisense nucleic acid molecules which hybridise under high stringency hybridisation conditions to nucleic acid molecules encoding the OmCI protein. High stringency hybridisation conditions are defined herein as overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C.

In a preferred embodiment, a label capable of being detected is attached to these antisense nucleic acid molecules. Preferably, the label is selected from the group consisting of radioisotopes, fluorescent compounds and enzymes.

The invention also includes transformed or transfected prokaryotic or eukaryotic host cells comprising a nucleic acid molecule, an antisense nucleic acid molecule or a vector as defined above. Where the host cells are prokaryotic cells, they preferably *E. coli* cells. Preferred eukaryotic host cells include eukaryotic yeast cells and mammalian cells.

The invention also provides a method for preparing a complement inhibitor molecule, as defined above, which comprises culturing a host cell containing a nucleic acid molecule according to the invention under conditions whereby the protein is expressed and recovering the protein thus produced. Preferably, the host cell is a yeast cell.

As discussed above in connection with functional equivalents, OmCI is believed to be a member of the lipocalin family of proteins and may exert part of its effect by binding an unidentified small ligand. Other complement inhibitor molecules of the invention and functional equivalents thereof may also exert their inhibitory effects of the pathways of complement activation by binding small ligands. The identification of these naturally-occurring ligands is desirable as they may themselves act as agonists or antagonists of the classical and/or alternative pathways of complement activation. Such naturally-occurring ligands may themselves be useful in the treatment of diseases associated with abnormally high or low complement pathway activation or may be useful starting points for the development of synthetic ligands for the treatment of such diseases. Alternatively, naturally-occurring ligands may be useful targets for the development of additional complement inhibitor molecules that bind to them. According to a further aspect of the invention, there is provided a method of identifying a ligand of a complement inhibitor molecule or a functional equivalent thereof as described previously comprising the steps of: (a) contacting the complement inhibitor molecule or functional equivalent thereof with a candidate ligand; and (b) detecting the formation of a ligand-complement inhibitor molecule complex.

Any candidate ligand may be used in this method. The candidate ligand may be isolated from, for example, cells, cell-free preparations, chemical libraries or natural product mixtures. Once naturally-occurring ligands of the complement inhibitor molecules have been identified, it may be desirable to design small synthetic molecules which mimic the tertiary structure of the naturally-occurring ligands. The ability of such synthetic molecules to bind to the complement inhibitor molecules can also be tested using the method of the invention.

The complement inhibitor molecule that is used in this method may be free in solution, affixed to a solid support, borne on a cell surface or located intracellularly. For example, the complement inhibitor molecule may be affixed to a solid support, with the candidate ligand being added subsequently. Alternatively, one or more candidate ligands may be affixed to a solid support and brought into contact with the complement inhibitor molecule.

The step of detecting the formation of a complex between the candidate ligand and the complement inhibitor molecule may be carried out by means of a label directly or indirectly associated with the candidate ligand or in an assay involving competition with a labelled competitor. In another embodiment, competitive screening assays may be used, in which neutralising antibodies that are capable of binding the complement inhibitor molecule specifically compete with a candidate ligand for binding. In this manner, the antibodies can be used to detect the presence of any test compound that possesses specific binding affinity for the polypeptide.

The method of the invention may employ high throughput screening techniques known in the art to screen multiple candidate ligands simultaneously for the ability to bind to a complement inhibitor molecule. For example, WO84/03564 discloses synthesising large numbers of different candidate ligands on a solid substrate, which may then be reacted with the complement inhibitor molecule of the invention and washed. Whether or not the complement inhibitor molecule has bound to the candidate ligands may then be detected using methods that are well known in the art.

The invention also provides a ligand of a complement inhibitor molecule identified or identifiable by the methods described above. Where the complement inhibitor molecule is an OmCI protein or a functional equivalent thereof, it is postulated that the ligand may be a small molecule that binds to C5 or to a C5 convertase or to a component of the MAC.

According to a further aspect of the invention there is provided a composition comprising a complement inhibitor molecule, a fusion protein comprising a complement inhibitor molecule, a nucleic acid molecule comprising a nucleic acid sequence encoding a complement inhibitor molecule, or a ligand of a complement inhibitor molecule, according to the above-described aspects of the invention, in conjunction with a pharmaceutically acceptable carrier. In particular, there is provided a composition comprising an OmCI protein or a functional equivalent thereof, a fusion protein comprising an OmCI protein or a functional equivalent thereof, a nucleic acid molecule comprising a nucleic acid sequence encoding an OmCI protein or a functional equivalent thereof, or a ligand of an OmCI protein or a functional equivalent thereof in conjunction with a pharmaceutically acceptable carrier.

The term "pharmaceutically acceptable carrier", as used herein, includes genes, polypeptides, antibodies, liposomes, polysaccharides, polylactic acids, polyglycolic acids and inactive virus particles or indeed any other agent provided that the excipient does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. Excipients may enable the pharmaceutical compositions to be formulated into tablets, pills, dragees, capsules, liquids, gels, syrups, slurries, suspensions to aid intake by the patient. A thorough discussion of pharmaceutically acceptable carriers is available in Remington's Pharmaceutical Sciences (Mack Pub. Co., N.J. 1991).

The composition may be used as a vaccine composition and may thus optionally comprise an immunostimulating agent, for instance an adjuvant. According to a further aspect of the invention, there is provided a process for the formulation of a vaccine composition comprising bringing a complement inhibitor molecule according to the above-described aspects of the invention, such as an OmCI protein or a functional equivalent thereof, into association with a pharmaceutically-acceptable carrier, optionally with an adjuvant. Suitable adjuvants are well-known in the art and include oil-in-water emulsion formulations, saponin adjuvants, Complete Freund's Adjuvant (CFA) and Incomplete Freund's Adjuvant (IFA) and other substances that act as immunostimulating agents to enhance the effectiveness of the composition.

According to a further aspect, the present invention provides a complement inhibitor molecule, a fusion protein comprising a complement inhibitor molecule, a nucleic acid molecule comprising a nucleotide sequence encoding a complement inhibitor molecule, or a ligand of a complement inhibitor molecule, as described above, for use in therapy.

The invention also provides a method of treating an animal suffering from a complement-mediated disease or disorder or preventing an animal developing a complement-mediated disease or disorder comprising administering to said animal a complement inhibitor molecule, a fusion protein comprising a complement inhibitor molecule, a nucleic acid molecule comprising a nucleotide sequence encoding a complement inhibitor molecule, a ligand of a complement inhibitor molecule, or a pharmaceutical composition according to the above-described aspects of the invention in a therapeutically or prophylactically effective amount.

Preferably, said animal is a mammal, more preferably a human.

The term "therapeutically effective amount" refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg (mass of drug compared to mass of patient) to 50 mg/kg, preferably 0.05 mg/kg to 10 mg/kg. Compositions may be administered individually to a patient or may be administered in combination with other agents, drugs or hormones.

The invention also provides the use of a complement inhibitor molecule, a fusion protein comprising a complement inhibitor molecule, a nucleic acid molecule comprising a nucleotide sequence encoding a complement inhibitor molecule, or a ligand of a complement inhibitor molecule according to the invention in the manufacture of a medicament for treating or preventing a complement-mediated disease or disorder.

The complement inhibitor molecules of the invention, and in particular the OmCI protein and functional equivalents thereof, have potential clinical uses in the treatment of all pathological conditions in which complement plays a role (Sahu and Lambris, 2000).

Preferred complement inhibitor molecules according to the invention, such as the OmCI protein and functional equivalents thereof, inhibit the classical and alternative complement pathways via inhibition of C5 cleavage by the C5 convertases of both the classical and alternative pathways. Specific inhibition of C5 cleavage by both C5 convertases blocks all three pathways of complement activation leading to the generation of C5a and MAC but preserves the immune clearance and opsonisation functions of complement which depend on C3b. Such a profile may be useful for therapeutic intervention in certain diseases such as Alzheimer's Disease, rheumatoid arthritis, glomerulonephritis and delayed-type hypersensitivity disorders (Kohl, 2001).

For example, in a mouse model of Alzheimer's disease (AD), which is associated with prominent brain inflammation (that may be partly mediated by complement), inhibition of C3 increased the deposition rate of beta-amyloid plaques (Wyss-Coray et al., 2002). Therefore inhibiting C5, but not C3, in may be beneficial in the treatment of AD.

Research into the role of C5 convertases reveals that complement inhibitor molecules of the invention which inhibit cleavage of C5 by C5 convertases, such as the OmCI protein and functional equivalents thereof, will also be useful in the treatment of a wide variety of other diseases and disorders. Since no natural inhibitors of the C5 convertases have been reported, researchers have up until now targeted this step by developing inhibitory anti-C5 antibodies, inhibitory RNA aptamers and synthetic peptides that target the C5a receptor (reviewed in Sahu and Lambris, 2000). Early studies, using the anti-C5 mAb BB5.1 (Frei et al., 1987) have clearly established the pathological role of C5a and the MAC in various disease models including immune complex nephritis (Wang et al., 1996), collagen induced arthritis (Wang et al., 1995), myocardial ischemia and reperfusion (Vakeva et al., 1998) and cardiopulmonary bypass patients (Rollins et al., 1998). The anti-05 mAB (18A10) has been shown to improve neural graft survival in rats (Ciccheti et al., 2002).

The complement inhibitor molecules of the invention that inhibit the classical and alternative complement pathways by inhibiting the cleavage of C5 by the C5 convertases of both pathways, such as the OmCI protein and functional equivalents thereof, will therefore be of use in the treatment of these diseases and disorders in three key areas: (1) control of autoimmune diseases such as rheumatoid arthritis; (2) reduction of tissue damage due to complement following surgery; and (3) suppression of tissue rejection particularly in the field of transgenic organ transplantation.

The pathology of autoimmune diseases such as rheumatoid arthritis and glomerulonephritis has many causal factors. The classical pathway of complement activation has a role in both diseases due to the presence of auto-antibodies that result in IgG and IgA antibody-antigen immune complexes within synovial fluid and glomerulus (Daha, 1993) which cause inappropriate activation of complement and tissue damage. Over-expression of soluble Crry (CR1 mouse homologue) protects transgenic mice from antibody-induced acute renal failure (Schiller et al., 2001). Rheumatoid arthritis immune complexes are complicated by the presence of IgM rheumatoid factors which can impede complement mediated inhibition of immune precipitation (Jarvis et al, 1993) and by decreased protection of synovial cells against cellular effects and lysis mediated by MAC (Kontinnen, 1996). C5 acting through the alternative complement pathway appears to have a crucial role in the K/B×N murine model of rheumatoid arthritis (Solomon et al., 2002). The complement inhibitor molecules of the invention, such as the OmCI protein and functional equivalents thereof, will thus be useful in the treatment of these autoimmune diseases.

Complement activation causes decrements in the myocardial function and increased coronary reperfusion pressure and lymphatic flow rate. Many of these changes may be mediated by the MAC (Homeister, 1992). Soluble CR1 protein produced by recombinant DNA technology is effective in inhibiting complement activation and consequent inflammatory activities in a rat model of reperfusion injury of transient myocardial ischaemia (Weisman et al., 1990). Crry reduces ischaemia reperfusion injury to mouse intestine (Rehrig et al., 2001). In humans, C5 inhibition by single chain humanised antibody h5G1.1-ScFV significantly attenuates postoperative myocardial injury, cognitive deficits and blood loss in patients undergoing cardiopulmonary bypass (Fitch et al, 1999). The complement inhibitor molecules of the invention which inhibit the activity of the C5 convertases of the classical and alternative pathways will thus be useful in the prevention and treatment of postoperative myocardial injuries such as reperfusion injuries.

There is ongoing interest in classical and alternative complement inhibitors which may be effective in hyperacute allo- and xenograft organ (heart and liver) rejection (Diamond et al., 1995; Thomas et al., 1996; Pratt et al., 1996; Tanaka et al., 1996; Fiorante et al., 2001; Bao et al., 2002). The major immunological barrier to xenotransplantation between man and pig is a rapid rejection process mediated by preformed natural antibodies and complement i.e. by classical pathway activation. Xenogeneic organ grafts are especially susceptible to complement mediated injury because complement regulatory proteins, which normally protect cells from injury, function poorly in the regulation of heterologous complement. The complement inhibitor molecules of the invention will thus be useful in the prevention of transplant rejection. The OmCI protein and functional equivalents thereof will be particularly useful in the prevention of transplant rejection since the OmCI protein inhibits the C5 convertases of a wide range of mammalian species (rodent and primate examined to date).

The anaphylotoxin, C5a, which is produced during the conversion of C5 by C5 convertases has been found to be involved in sepsis, immune complex disease and delayed—type hypersensitivity. The OmCI protein and functional equivalents thereof, as well as other complement inhibitor proteins of the invention that inhibit C5 convertases will be useful in the treatment of these disorders. The OmCI protein and functional equivalents thereof might prove useful as an adjuvant therapy during xenotranplantation by preventing the formation of C5a and stopping deposition of the MAC that may cause upregulation of tissue factor and P-selectin expression in animal models of transplantation (Fecke et al., 2002).

Other possible specific uses include: (1) prevention of platelet activation by complement during storage of platelet concentrates (Miletic and Popovic, 1993), (2) activation of complement by biomaterial surfaces during blood transfusion, (3) fertility treatment (Bedford and Witkin, 1983) and (4) protection of gene therapy retroviral vectors from lysis by natural antibody and complement during gene therapy (Rollins et al., 1996).

Haematophagous arthropods, such as ticks, are extremely effective as transmitters of disease. Conventionally, techniques to control tick populations have used the treatment of animals with chemicals such as acaracides. This strategy has resulted in the development of resistant ticks, meaning that new classes of chemicals must be introduced. Furthermore, the chemicals have little residual effect, meaning that they must be applied frequently. A second approach is to breed for tick-resistant animals, but the degree of resistance that results is far from ideal.

In an effort to combat parasite-transmitted diseases, a number of attempts have been made to immunise animals against ticks using extracts of whole ticks or of tick gut. Certain reports have used recombinant tick proteins (see, for example, International patent application WO88/03929). However, despite such developments, the only commercially-available tick vaccines are active only against the adult stage of *B. microplus* ticks and show variation in efficacy depending on the geographical location of this species.

According to a still further aspect of the present invention, there is provided a method of vaccinating an animal against a disease or disorder transmitted by a haematophagous arthropod, comprising administering to said animal a complement inhibitor molecule, a fusion protein comprising a complement inhibitor molecule, a nucleic acid molecule encoding a complement inhibitor molecule, or a composition according to the above-described aspects of the invention.

Suitable candidates for vaccination include humans and domesticated animals such as cattle, goats, sheep, dogs, cats and other animals which require protection against haematophagous arthropods, especially ticks, and the infections they transmit. The vaccine may be administered singly, or in combination with other immunogens. The method of this aspect of the invention may be used to vaccinate the animal against any disease or disorder transmitted by the haematophagous arthropod. Preferably, the haematophagous arthropod is a tick, preferably *O. moubata*. Diseases and disorders transmitted by ticks of the genus *Ornithodoros* include relapsing fever (Borreliosis) and West Nile virus of man, and African swine fever virus of pigs.

The invention further provides for the use of a complement inhibitor molecule according to the above-described aspects of the invention as a diagnostic tool. The identification of the complement inhibitor molecules of the invention will enable researchers to study the effects of simultaneous inhibition of both the classical and alternative complement pathways. In particular, the identification of the OmCI protein will enable researchers to study the effects of simultaneous inhibition of both the classical and alternative complement pathways via C5 convertase inhibition.

The invention also provides a method for inhibiting the classical and alternative complement pathways in a cell, tissue or non-human organism comprising administering to said cell, tissue or organism, a complement inhibitor molecule, a fusion protein comprising a complement inhibitor molecule, or a nucleic acid molecule encoding the complement inhibitor molecule, according to the above-described aspects of the invention. In particular, the invention provides a method for inhibiting the C5 convertase activity in a cell, tissue or non-human organism, comprising administering to said cell, tissue or organism, an OmCI protein or functional equivalent thereof, a fusion protein comprising an OmCI protein or functional equivalent thereof, or a nucleic acid molecule encoding an OmCI protein or functional equivalent thereof. This method will enable researchers to elucidate the role of C5 in various diseases and disorders. For example, it has been suggested that C5 may play a positive role in the prevention of asthma (Kohl, 2001). The C5 convertase inhibitors of the invention can be used to determine whether that is the case.

Various aspects and embodiments of the present invention will now be described in more detail by way of example. It will be appreciated that modification of detail may be made without departing from the scope of the invention.

BRIEF DESCRIPTION OF FIGURES

FIG. 4: Primary sequence of OmCI. Signal sequence underlined. Cysteine residues in bold type. Nucleotide and amino acid number indicated at right. The nucleic acid sequence (SEQ ID NO: 1) and the amino acid sequence (SEQ ID NO: 2) are depicted.

EXAMPLES

Materials and Methods

Materials

Figure 1:
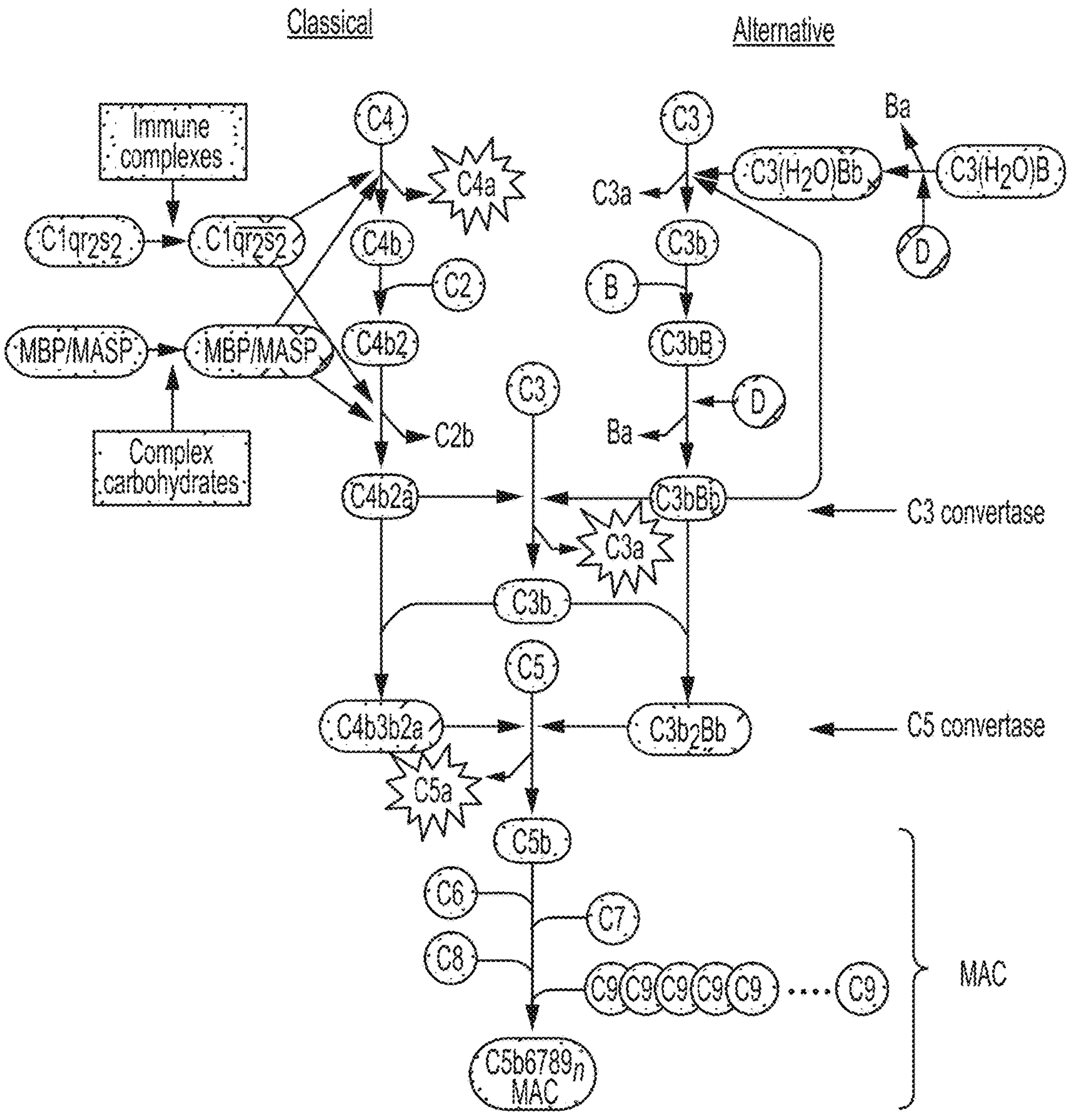
FIG. 1: Schematic diagram of classical and alternative pathways of complement activation. Enzymatic components, dark grey. Anaphylatoxins enclosed in starbursts.

Sheep and rabbit red blood cells were from Tissue Culture Services, Haemolysin, pooled normal human sera (NHS) and depleted sera were all obtained from Sigma. Guinea pig sera were from in house animals. Pure C3, C4, C5, C8 and C9, and factors B and D, were purchased from Calbiochem. Anti-human C3a rabbit polyclonal antisera was from Calbiochem and cobra venom factor (CVF) from Quidel. The C5a ELISA detection kit was purchased from Immuno-Biological Laboratories (IBL).

Ticks

*Ornithodorus moubata* ticks were reared according to Jones et al. (1988).

Salivary Gland Sample Preparation and Purification

Salivary glands were dissected under a microscope, rinsed briefly in cold PBS buffer (0.01M phosphate buffer and 0.15M NaCl pH 7.2) and transferred to Eppendorf vials standing in dry ice and stored frozen at −20° C. When needed, 30 pairs of salivary glands were defrosted and disrupted in 500 μl PBS using a 1 ml Dounce homogenisor. The homgenate was centrifuged at 15K RPM in a benchtop centrifuge and the supernatant (referred to as salivary gland extract, SGE) was collected and stored at −70° C., or tested for complement inhibitory activity and used for isolation of the active fraction.

Classical Pathway of Complement Haemolytic Assay (CH50)

Five ml of fresh sheep blood in Alsever's solution (1:1 vol/vol) were washed once in 50 ml Gelatin veronal barbital-EDTA (GVB-EDTA) and three times in 50 ml $GVB^{2+}$ buffer (GVB buffer with $Mg^{2+}$ and $Ca^{2+}$). The blood was diluted to a concentration of $1\times10^9$ cells $ml^{-1}$. The erythrocytes were sensitised using rabbit haemolysin, titrated as described (Coligan, 1994). Assays were carried in a total volume of 200 μl using 100 μl 1:40 of diluted NHS or guinea pig sera in $GVB^{2+}$ as a source of complement and 100 μl $2\times10^8$ sensitised erythrocytes (EA) in accordance with standard protocols (Giclas, 1994). SGE, native or recombinant OmCI (nOmCI or rOmCI) or PBS (1-5 μl) was added last, and the reactions incubated at 37° C. At the end of the timecourse (up to 32 min) whole cells were spun down 12000×g for 5 seconds and hemolysis measured spectrophotometrically at 412 nm (Coligan, 1994). All assays were carried out at least three times.

Alternative Pathway of Complement Hemolytic Assay (AH50)

Five ml of fresh rabbit blood in Alsever's solution (1:1 vol/vol) were washed three times in 50 ml GVB/Mg (10 mM) EGTA buffer by centrifuging at 1500×g for 10 mins between washes. The rabbit blood was diluted to $2\times10^8$ cells $ml^{-1}$. NHS was diluted in GVB/Mg EGTA buffer. The assay volume was made up to 150 μl with 50 μl prepared blood. 1-5 μl of SGE, PBS, native OmCI or recombinant OmCI was added to the reactions last, and the reactions incubated at 37° C. At the end of the timecourse (up to 60 min) whole cells were spun down 12000×g for 5 seconds and haemolysis measured spectrophotometrically at 412 nm (Coligan, 1994). All assays were carried out at least three times.

Lytic Assays Using Sera Depleted in Specific Complement Components

Depleted human sera were used in accordance with the manufacturer's instructions but the total volume of each reaction was reduced to 200 μl. Volumes and dilutions of pure complement components that gave 90% lysis were determined empirically. Reactions were incubated for 30 mins at 37° C. All assays were carried out at least three times.

Purification of *O. moubata* Complement Inhibitor (OmCI) from SGE

150 μl SGE were diluted in 5 ml 25 mM sodium phosphate buffer pH 6.8, 50 mM NaCl and loaded onto a 1 ml Q-SEPHAROSE™ HP cation exchange column (Pharmacia) at a flow rate of 1 ml/min. After washing with a further 10 column volumes of running buffer, bound proteins were eluted using a 40 min 0.05-0.75M NaCl gradient at a flow rate of 0.5 ml/min and monitored at 280 nm. One ml fractions were collected and 10 μl assayed for complement inhibitory activity in 200 μl total volume CH50 assays. Representative active and inactive fractions were concentrated to 50 μl using Centricon 3 filtration devices (Amicon), 2 ml PBS was added, the fractions were concentrated to 50 μl again and 1.5 μl of each was run on a 4-12% Tris-Tricine denaturing SDS gel (Invitrogen). Five μl per lane of both active and inactive fractions were run on a pH 3-7 IEF gel (Invitrogen) and electroblotted to IMMOBILON™ P (Mllipore) using 0.7% acetic acid. The membrane was stained with Ponceau-S, and major bands excised and eluted in 200 μl, 50 mM Tris pH 8, 2% TRITON™ X-100 (polyethylene glycol tert-octylphenyl ether) by vortexing for 1 min and centrifuging for 10 min at 15 K rpm three times. The TRITON™ X-100 was removed by repurifying the proteins on Q-SEPHAROSE™ HP columns using the conditions described above. After Centricon 3 concentration and buffer exchange to PBS, samples were assayed for complement inhibitory activity and examined on 4-12% gels or subjected to HPLC fractionation and protein sequence analysis.

Detection of C3a Production During Haemolytic Assays

CH50/AH50 assays were set up in a total volume of 200 μl using a 1:80 final dilution of NHS or guinea pig sera with or without native OmCI. Reactions placed at 37° C. were removed from the waterbath at specified time points, then spun at 12000 g for 10 seconds and the supernatant removed for subsequent analysis by immunoblotting. 10 μl of each reduced supernatant sample was electrophoresed on 4-12% Bis-Tris gel run with MES running buffer (Invitrogen) then transferred to nitrocellulose. Confirmation of equal loading and even transfer to all lanes was judeged by the intensity of the serum albumin band following Ponceau staining. C3a cleavage from C3 was detected by immunoblot using anti-human C3a rabbit monospecific antisera (Calbiochem). The nitrocellulose membrane was blocked overnight with phosphate buffered saline 0.1% TWEEN® (polysorbate 20), 5% non-fat dried milk (PBS™). This buffer was used for all subsequent dilutions and washing steps unless indicated otherwise. Anti-C3a antisera was diluted 1:500 and incubated with the membrane for 2 h. The membrane was then washed twice for 20 minutes before adding 1:3000 dilution of anti-rabbit alkaline phosphatase conjugate (Sigma) in PBS™. After another 2 h incubation the membrane was washed twice for 5 minutes, rinsed briefly in water and 10 ml BCIP/NBT purple liquid alkaline phosphatase substrate (Sigma) added.

Detection of C5a Production During Haemolytic Assays

Haemolytic assays were performed as described for detection of C3a. A C5a ELISA kit (IBL) was used to detect cleavage of C5a from C5. To prevent cross-reaction with uncleaved C5, the C5 present in the supernatant from the haemolytic assays was precipitated using the reagent provided by the kit manufacturers. The measuring range of the kit extends from 0.1 to 10 μg/L. The lower limit of detection is 0.02 μg/L.

Decomplementation of Sera with Cobra Venom Factor (CVF)

0.25 μg CVF (0.25 μg/μl stock) and either 1 μl native OmCI or 1 μl PBS was added to 5 μl human sera and incubated for 1 hour at 37° C. Half the CVF treated sera was added to 97.5 μl $GVB^2$ and 100 μl EA. After incubation for 20 mins at 37° C. percentage lysis and concentration of C5a (see above) in reaction supernatants were determined.

HPLC of Active Fraction, Protein Sequence Analysis and Tryptic Digestion

Twenty μl of the active fraction eluted from the IEF resolved protein was run on a Jupiter C4 column/150×1.0 mm, and a gradient of 10-40% acetonitrile (ACN) with 0.1% trifluoroacetic acid (TFA), flow rate 1 ml/min with 0.5% ACN/min increments, and monitored at 215 nm. The four close running peaks at c.53 min were transferred to Immobilon-P membrane and sequenced using an Applied Biosystems Mini-Blott cartridge. Twenty five cycles were performed on each protein.

For sequence analysis of tryptic digestion products, the major peak at 53 min (comprising all four peaks observed in the first HPLC separation) was dried down in a SpeedVac and redissolved in 6M guanidine 0.5M Tris pH 8.0, then reduced and alkylated using 4-vinylpyridine. It was then re-run on the same Jupiter C4 column. No change in retention time was noted. The major peak was dried in SpeedVac and redissolved in 0.1M ammonium bicarbonate pH 8.1. Ten μl of Pierce immobilised trypsin was added and the mixture incubated at 37° C. for 5 hours with intermittent mixing. The mixture was then spun at 10K rpm and the supernatant was loaded on a 173a microblotting HPLC (Aquapore C18 column/100×0.5 mm). Peaks of interest were excised from the membrane and sequenced. Fifteen cycles were performed on each protein.

Construction of *O. moubata* cDNA Library

Sixty pairs of *O. moubata* salivary glands collected from nymphs after their 3rd or 4th feed were excised as described above and placed in 1 ml RNAlater® (Ambion) (in place of PBS) and stored at −20° C. mRNA was isolated using the FASTTRACK™ 2.0 mRNA isolation kit (Invitrogen) and cDNA was synthesised using a Stratagene cDNA synthesis kit (Cat#200401-5). After fractionation into large and small cDNAs on a sepharose CL-2B column, the ethanol precipitated cDNA pellets were each resuspended in 3.5 μl $ddH_20$. cDNA yields were approximately 3.0 ng/μl and 5 ng/μl for the large and small molecules, respectively. All of the remaining large and small cDNAs were ligated into the Stratagene UniZAP XR phage vector (Cat. #237211) and packaged with GIGAPACK® III Gold packaging extract. There were 11500 primary plaques in the large cDNA library and 480500 primary plaques in the small cDNA library. After amplification, the titres of the large and small libraries were $1.5\times10^8$ pfu/ml and $4\times10^9$ pfu/ml, respectively.

Twenty plaques from each library were picked into 0.5 ml SM buffer (O. 1M NaCl, 8 mM $MgS0_4$, 50 mM TRIS.HCl pH 7.5, 0.01% gelatin) 1% chloroform and eluted from agarose plugs by vortexing. Phage insert sizes were examined by PCR using T7 (T7 5'T AA TAC GAC TCA CTA TAG 3': SEQ ID NO: 10) and T3 (5'AAT TAA CCC TCA CTA AAG 3': SEQ ID NO: 11) primers. Each 100 μl reaction comprised 2 μl eluted phage, 2 μl OmM dNTPs, 2 μl of each primer (from stocks of 0.5 m/ml), 10 μl 1O×REDTaq® (Sigma) PCR reaction buffer (100 mM Tris-HCl pH 8.3, 500 mM KCl, 11 mM $MgCl_2$, 0.1% gelatin), 3 μl REDTaq® (Sigma) DNA polymerase (1 unit/μl in 20 mM Tris-HCl, pH 8.0, 100 mM KCl, 0.1 mM EDTA, 1 mM DTT, 0.5% TWEEN® (polysorbate 20), 0.5% IGEPAL® CA-630 (octylphenoxypolyethoxyethanol), inert dye, 50% glycerol) and 79 μl $ddH_2O$. Thermal cycling (Hybaid Touchdown thermal cycler) parameters were IX 94° C. 4 min, 30×94° C. 1 min, 48.5° C. 45 s, 72° C. 90 s, and 1×72° C. 5 min. Agarose gel electrophoresis of the PCR products showed that large library inserts were ≥1000 base pairs and small library inserts ≥1000 base pairs.

Cloning cDNA Encoding Complement Inhibitor

The N-terminal sequences determined for the two major peaks eluting at 53 min from the HPLC were used to design a degenerate primer (OF4) for use with the T7 primer (which binds to the UniZAP XR vector), to amplify the cDNA encoding the complement inhibitor. The sequence of OF4 was 5' GTAC WSN GGN WSN GAR CCN GT 3' (where: N=A or C or G or T; R=G or A; S=G or C; and W=A or T) (SEQ ID NO: 12). The 100 μl reaction comprised 3 μl large or small cDNA library, 3 μl mM dNTPs, 2 μl T7 and 4 μl OF4 (from stock of 0.5 μg/ml), 10 μl IO×REDTaq® PCR reaction buffer, 3 μl REDTaq® DNA polymerase and 75 μl $dH_20$. Thermal cycling parameters were IX 94° C. 4 min, 30×94° C. I min, 48.5° C. 45 s, 72° C. 90 s, and IX 72° C. 5 min.

Agarose gel electrophoresis revealed a range of PCR products. Two products derived from the OF4 primer were purified using a Qiaex II gel extraction kit (Qiagen) and sequenced with an ABI PRISM™ dye terminator cycle sequencing ready reaction kit and ABI sequencer (Perkin Elmer).

Conceptual translation of the largest (c.500 bp) and most intense PCR product, derived from the small cDNA library using primer OF4 with T7, revealed a significant BlastX (Altschul et al., 1997) match with the C-terminal sequence of the *O. moubata* platelet aggregation inhibitor moubatin (Waxman and Connolly, 1993). The sequence extended beyond the stop codon of the cDNA encoding the peptide. A reverse primer (ORI 5' GGG AGG CTT TCT GTA TCC 3'; SEQ ID NO: 13) matching the region beyond the stop codon was used with the T3 primer (which binds to the UniZAP XR vector) to obtain the 5' end of the cDNA. The 650 bp PCR product was cloned into the pGEM®-T Easy vector (Promega) then sequenced using additional primers OR3 5'CGT CCA ATC GOT TGA AG 3' (SEQ ID NO: 14) and OF6 5' GAC TCG CAA AGT CAT CAC 3' (SEQ ID NO: 15).

Sequence Analysis

Analyses were carried out using the GCG suite of programs (Wis. Package Version 10.1, Genetics Computer Group (GCG), Madison, Wis.) and also the ExPASy (Expert Protein Analysis System) proteomics server of the Swiss Institute of Bioinformatics. Sequences were compared with the GenBank non-redundant (NR) protein database using the BlastX program (Altschul et al., 1997) and searched against the Pfam (Bateman et al., 2000) and SMART (Schultz et al., 2000) protein domains. Multiple sequence alignment was performed with Clustal X (Jeanmougin et al., 1998).

Yeast Expression and Purification of OmCI

The OmCI coding region was amplified by means of the polymerase chain reaction (PCR; 95° C. for 30", 50° C. for 30", 72° C. for 30"; 18 cycles), using the forward primer OMIY (5'-ATAGAGCTCAAAATGCTGGTTTTGGTGACC-3') (SEQ ID NO: 16) and the reverse primers OR7a (5'ACTGAGCGGCCGCCTAGTGATGGTGATGGTGAT GACCGCAGTCCTTGAGATGGGG 3' (SEQ ID NO: 17) for his-tagged products) or OR6 (5' ACTGAGCGGCCGC-CTAGCAGTCCTTGAGATGGGG 3' (SEQ ID NO: 18) non-tagged product). The primers have built-in restriction sites, such that a Sac I site is added upstream of the start codon and a Not I site downstream of the stop codon. The product was ligated between the Sac I and Not I sites of the pMETα C transfer vector (Invitrogen). The plasmid—amplified in XL I-Blue cells (Stratagene)—was transformed into the *Pichia methanolica* strains pMAD16 and pMAD11, according to the instructions of the supplier (Invitrogen). Positive clones were grown in Buffered Dextrose-complex Medium BMDY, and protein expression was induced in Buffered Methanol-complex Medium. Protein expression in the supernatant and cells of 6 positive clones was assayed every 24 hours for 5 days by CH50 lytic assay.

After 96 hours incubation, 500 ml yeast cell media was centrifuged at 6370 g for 15 mins and the inhibitor precipitated from the supernatant by addition of 30% (w/v) PEG-8000 and stirring on ice for 1 hour. Following centrifugation at 23700 g for 1 hour the protein pellet was resuspended in 50 ml 25 mM sodium phosphate buffer pH 6.8, 50 mM NaCl before centrifuging at 6,000 rpm to remove insoluble material. The clarified solution was applied to a 1 ml 0-SEPHAROSE™ HP cation exchange column and complement inhibitory activity of fractions determined as described above. Active fractions were pooled and exchanged to 300 μl PBS using Centricon 3 filtration devices (Amicon), centrifuged at 18900 g for 10 minutes then applied to a Superdex™ 75 column (Pharmacia) at a flow rate of 0.5 ml/min using 20 mM Tris pH 7.6, 200 mM NaCl as running buffer. 0.5 ml fractions were monitored at 280 nm and collected for 30 minutes. 5 μl of each fraction was assayed for inhibitory activity and active fractions exchanged to PBS before visualisation by denaturing SDS-PAGE.

Purified rOmCI was treated with peptide N-glycosidase F (PNGaseF) in accordance with the manufacturer's instructions (New England Biolabs). Deglycosylated rOmCI was repurified by gel filtration as described above. Five inhibitory fractions were identified by CH50 and 15 μl of each was run on SDS PAGE under denaturing and non-denaturing conditions.

Thermostability and pH Stability of Native OmCI

The minimal amount of native OmCI that inhibits classical pathway mediated cell lysis by c.90% at a 1:40 dilution of guinea pig serum was determined to be 25 ng in a total reaction volume of 100 μl. To examine thermostability, 1 μl native OmCI (250 ng) was diluted in 9 μl PBS. Samples were boiled for 0, 3, 9 or 27 min, cooled rapidly on ice, and 1 μl (25 ng) added to 100 μl CH50 assays (1:40 guinea pig serum dilution). To examine pH stability, 1 μl native OmCI (250 ng) was diluted in 9 μl 10 mM sodium acetate (pH 4.5 and 5.5), 10 mM Tris.Cl (pH 7 and 8.2) or 10 mM CAPS (pH 10 and 11) buffer. After incubation for 30 min at 37° C., 1 μl (25 ng) was added to 100 μl CH50 assays (1:40 guinea pig serum dilution). Controls included 1 μl of each of the buffers only in the presence and absence of 1:40 serum dilution. All assays were done in triplicate.

Method for Detection of C5 Binding to OmCI 0.5 μg native OmCI and 5 μg RaHBP2 were subjected to non-denaturing SDS-PAGE, then transferred to nitrocellulose and blocked overnight in PBS, 0.05% TWEEN® (polysorbate 20), 5% non-fat dried milk (PBS™). C3 and CS were labelled with $I^{125}$ using Iodogen in accordance with the manufacturer's instructions (Pierce). Blots were incubated with 2 μg $I^{125}$ labelled C3 (1440 kcpm/min), and 2 μg $I^{125}$ labelled CS (2160 kcpm/min) in 15 ml PBS™ for 4 hours at room temperature. After 3×20 min washes in PBS™ at room temperature the nitrocellulose membranes were dried, and autoradiogrammed.

For gel filtration chromatography, 0.07 μg $I^{125}$ labelled OmCI (1687 kcpm/min) was incubated with 2 μg pure C3 or C5, or 23.8 μl NHS or C3 or C5 depleted serum. PBS was added a total volume of 100 μl and the mixture incubated for 10 min before chromatography through a Superose 12 10/30 column at a flow rate of 1 ml/min PBS. 1 ml fractions were collected and cpm measured at set distance from a hand held Geiger counter.

Results

Purification and Identification of Active Fractions from *O. moubata* SGE

Figure 2A:
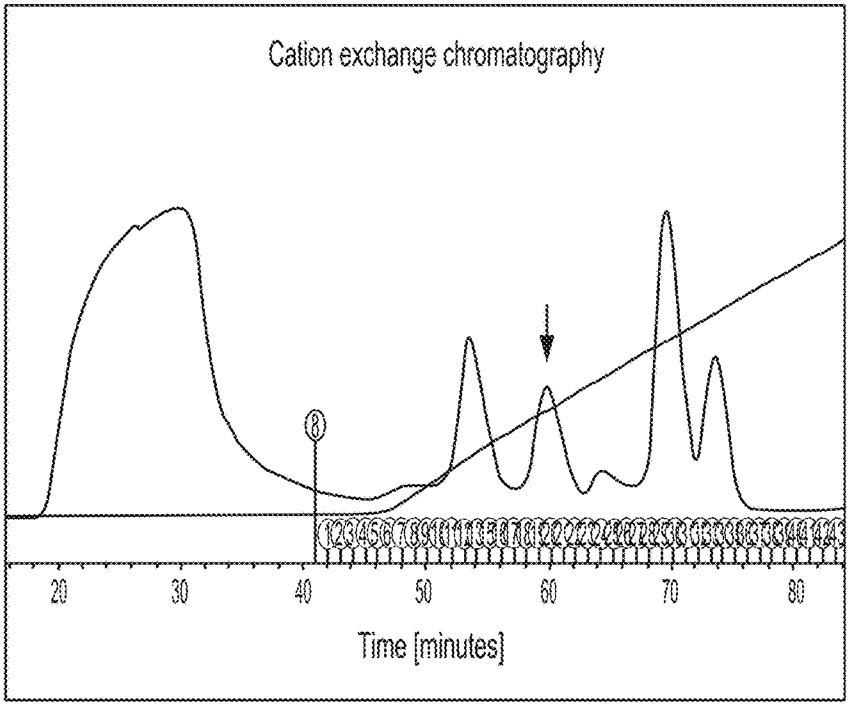
FIG. 2A: Purification of *O. moubata* complement inhibitor (OmCI). Cation exchange chromatography. Peak containing inhibitor indicated by arrowhead.
Figure 2B:
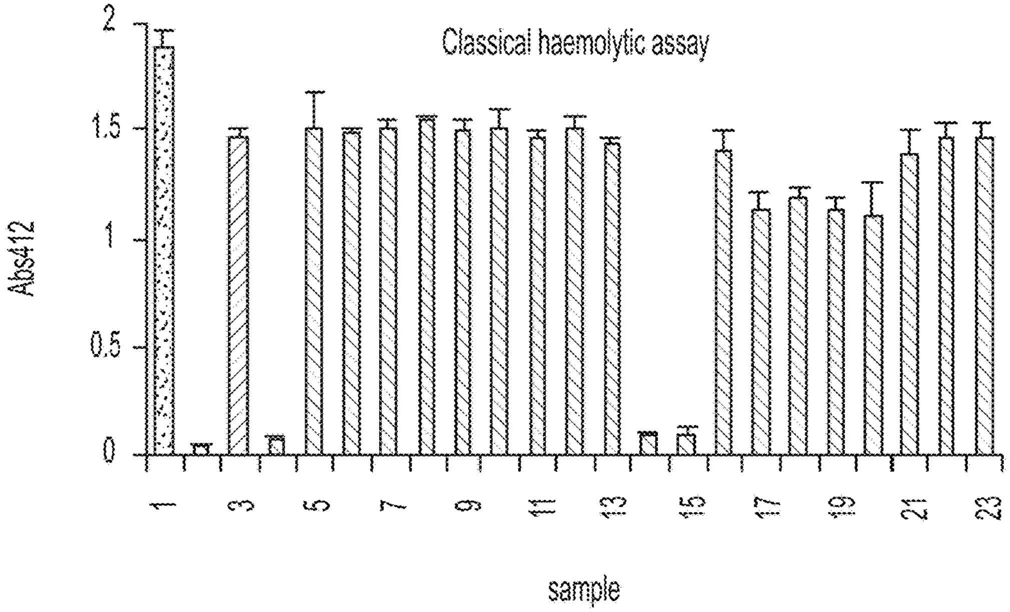
FIG. 2B: Purification of *O. moubata* complement inhibitor (OmCI). Classical haemolytic assay. Sample 1 (black bar), 100% lysis; sample 2, 0% lysis; sample 3, (cross-hatched bar) serum only; sample 4, serum plus 1 μl SGE; samples 5-23 (grey bars) serum plus 10 μl fractions 10-28 shown in FIG. 2A. Average of 3 replicates.
Figure 3A:
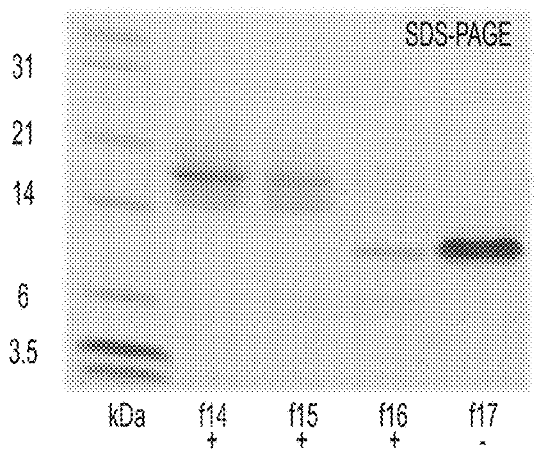
FIG. 3A: Analysis of purified OmCI by denaturing SDS-PAGE.
Figure 3B:
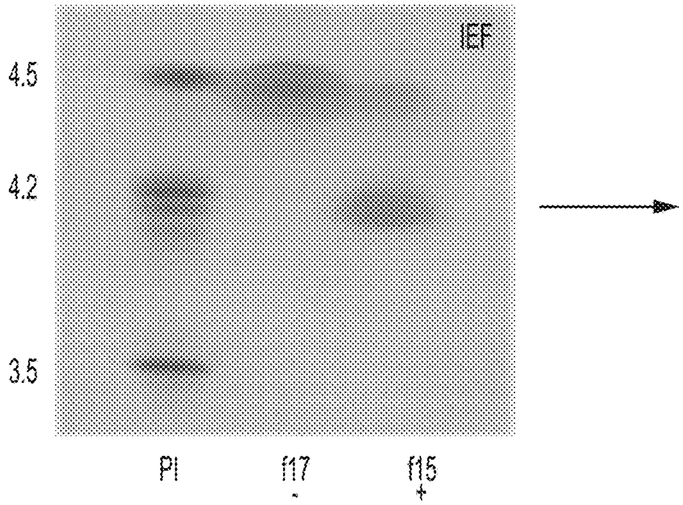
FIG. 3B: Analysis of purified OmCI by isoelectric focusing (IEF).
Figure 3C:
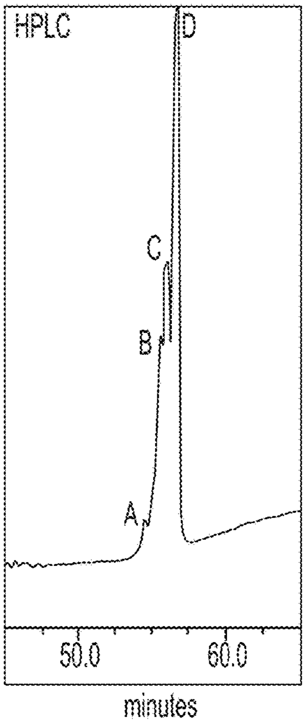
FIG. 3C: Analysis of purified OmCI by high pressure liquid chromatography (HPLC). Fractions f15 and f17 in FIG. 3A and FIG. 3B are the same. Fraction f15 was recovered and analysed by HPLC, FIG. 3C. Size markers and isoelectric point (PI) markers are indicated at left of FIG. 3A and FIG. 3B.

Following cation exchange chromatography, the active fraction eluted at 0.25M NaCl (FIGS. 2*a* and *b*, arrow). The active fraction a control fraction (FIG. 3*a*) were electroblotted from an IEF gel (FIG. 3*b*) to a PVDF membrane which was stained with Ponceau-S. The major bands were excised, eluted, repurified by cation exchange chromatography and assayed for complement inhibitory activity. Denaturing SDS PAGE showed the inhibitory activity to be associated with a triplet of proteins with masses of around 19 kDa (FIG. 3*a*). IEF showed the inhibitory activity to be associated with a single dominant band with a pI of approximately 4.2 (FIG. 3*b*, upperband carryover from fraction 17). HPLC of the PVDF eluted fraction revealed four adjacent peaks (FIG. 3*c*). A 17 amino acid N-terminal sequence (DSESDXSGSEPVDAFQA) (SEQ ID NO: 19) obtained from the largest peak (FIG. 3*c*, peak D) was used to design degenerate primers that generated a PCR product from *O. moubata* cDNA library which matched the N-terminal sequence.

Primary Structure of the cDNA Encoding OmCI

The sequence of the full-length clone shows that OmCI is 168 amino acids long (FIG. 4). The protein has an N-terminal secretion signal comprising the first 18 residues. N-terminal sequence analysis indicates the signal peptide cleavage site is between Ala18 and Asp19. The predicted molecular weight of the mature protein is 16.77 kDa and the isoelectric point 4.3. There are two predicted N-glycosylation sites (Asn78 and Asn102) and twelve potential phosphorylation sites (Ser 20, 22, 25, 84, 113, 115, 156, Thr90, Tyr17, 43, 111, 130, 162). However, such sites have a high probability of occurrence (protein kinase C, casein kinase II, and tyrosine kinase sites) and a site prediction may not necessarily indicate a genuine modification.

Figure 5:
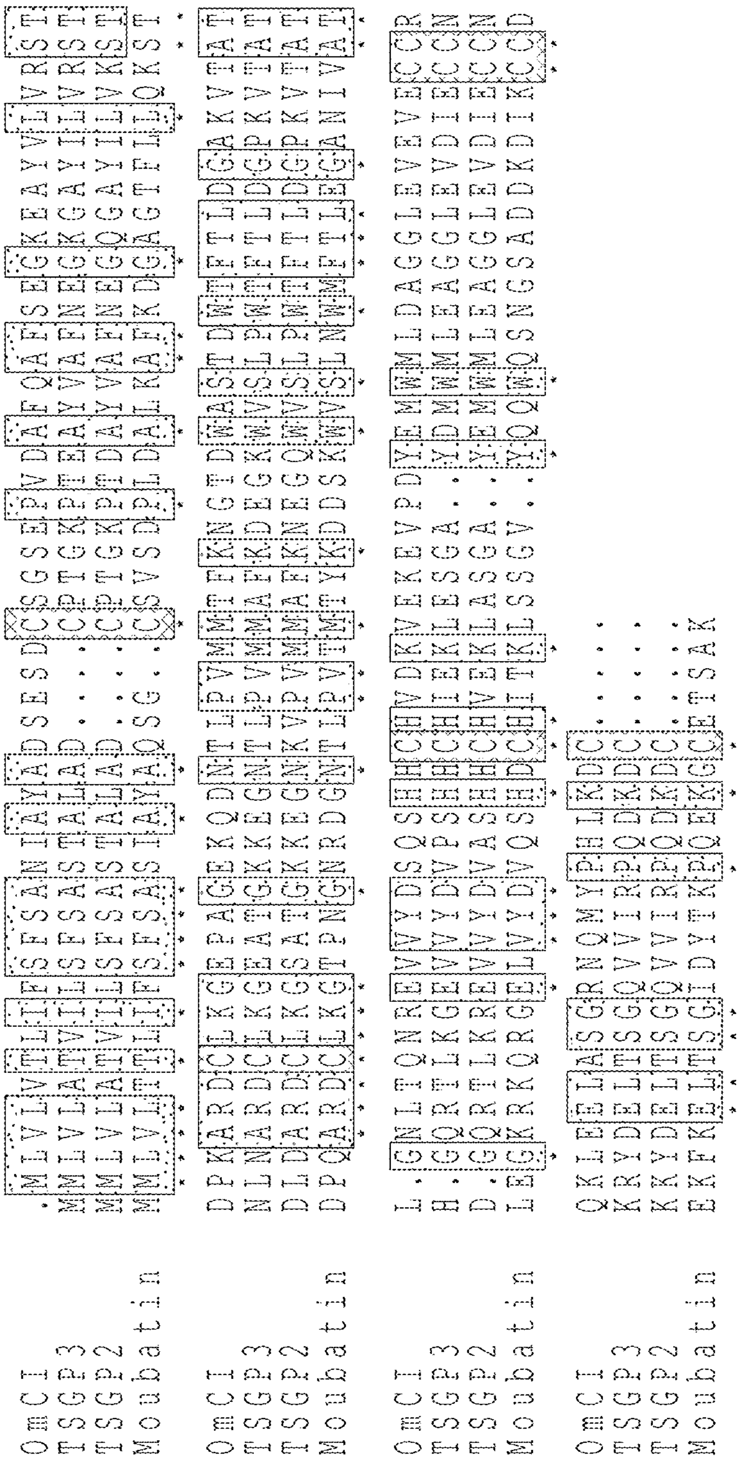
FIG. 5: Clustal X sequence alignment of OmCI with tick salivary gland proteins 2 and 3 (TSGP2 and 3) and moubatin. Identical residues are highlighted in grey (cysteines in black) and asterisked. The amino acid sequences are designated as follows: OmCI (SEQ ID NO: 6): TSGP3 (SEQ ID NO: 7): TSGP2 (SEQ ID NO: 8): and Moubatin (SEQ ID NO: 9).

The primary sequence of OmCI shows 58% identity to tick Salivary Gland Proteins 2 and 3 (TSGP2 and 3) of the soft tick *Ornithodorus savignyi* (Mans et al, 2001), and 49% identity to moubatin from *Ornithodorus moubata* (Waxman and Connolly, 1993). All the cysteine residues, and therefore presumably the disulphide bridging pattern, are conserved in these four proteins (FIG. 5). The alignment shows that OmCI has two obvious short amino acid insertions: SESD at the amino terminus and PD about two-thirds of the way through the sequence of the mature peptide (FIG. 5). The primary sequence does not have a significant match with any other any other sequences in public databases including the anti-complement protein of *I. scapularis* (Valenzuela et al., 2000). Moubatin, and TSGP2 and 3 are believed to be members of the lipocalin family of beta barrel forming proteins that include the histamine binding protein family of tick specific proteins (Paesen et al., 2000).

Expression and Purification of Recombinant (r) OmCI

Figure 6A:
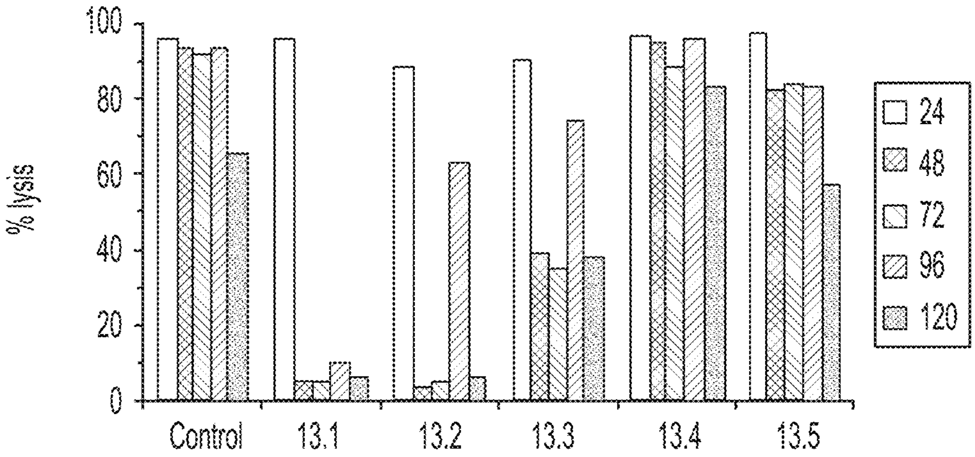
FIG. 6A: Inhibitory activity in supernatant of yeast clones with OmCI inserted into genome (13.1-13.5), and clone with vector only inserted into genome (control).
Figure 6B:
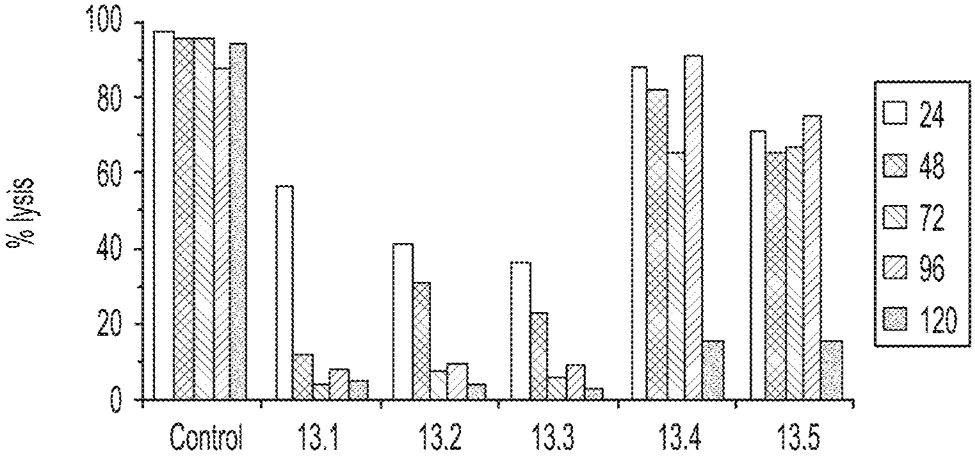
FIG. 6B: Inhibitory activity in cell pellet of yeast clones with OmCI inserted into genome (13.1-13.5), and clone with vector only inserted into genome (control).
Figure 7A:
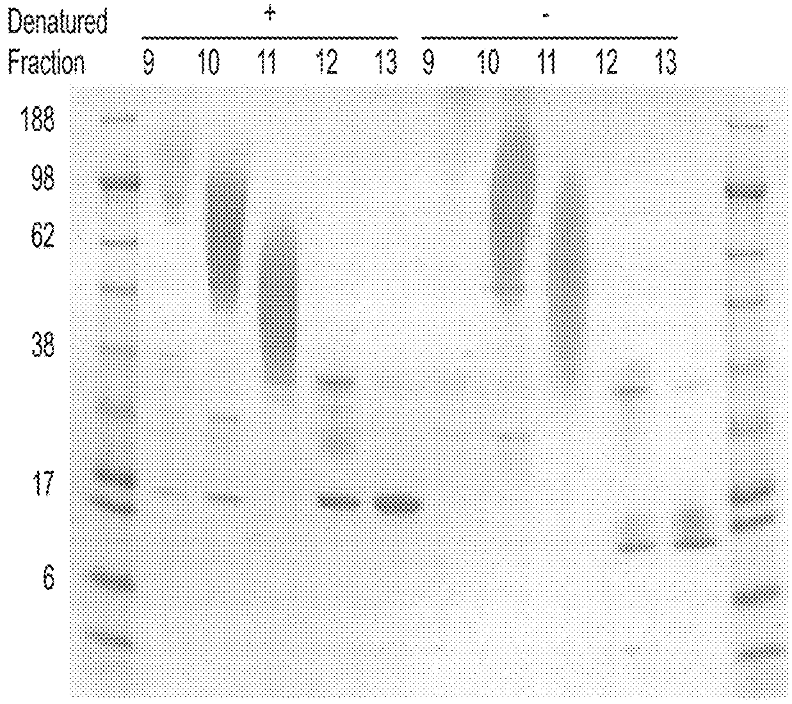
FIG. 7A: Expression of yeast cell expressed rOmCI. SDS PAGE of fractions 9-13 from Superdex-75 gel filtration column.
Figure 7B:
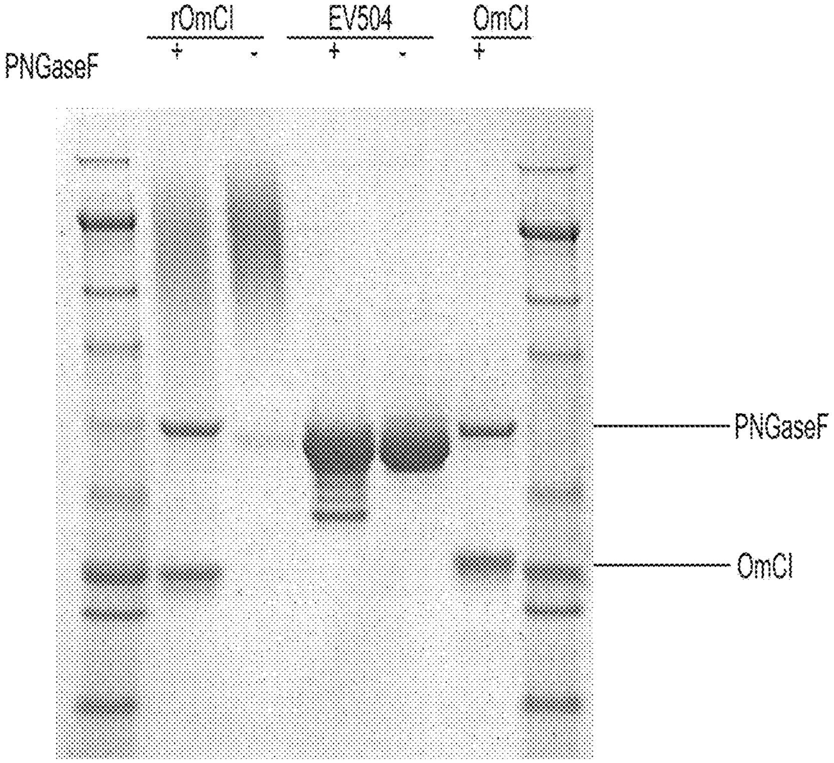
FIG. 7B: Deglycosylation of yeast cell expressed rOmCI. Effect of PNGaseF treatment on mobility of highly glycosylated rOmCI (fractions 9-11 in FIG. 7A). Arrows indicate PNGaseF (upper arrow) and native OmCI (lower arrow). EV504 is distantly related to OmCI and is known to be glycosylated. Size markers (kDa) indicated at left of panel.

The 6 positive yeast clones assayed exhibited variable levels of OmCI expression (FIGS. 6*a* and *b*). In all cases where expression was detected, inhibitory activity continually increased through to the final assay point on day 5. Approximately 90% of the expressed protein was in the supernatant (FIG. 6*b*). Clone 13.1 appeared to give the highest expression levels and was used for subsequent expression studies. Following PEG precipitation and two chromatography steps partially purified active rOmCI is present in heavily glycosylated (FIG. 7*a*, fractions 9, 10 and 11) and unglycosylated forms (FIG. 7*a*, fractions 12 and 13). The glycosylated form was shown to correspond to the unglycosylated form by treatment with PNGaseF (FIG. 7*b*). Glycosylated and unglycosylated or deglycosylated rOmCi and native OmCI are equally active in CH50 assays (data not shown). The final yield of rOmCi was approximately 0.3 μg/ml of media.

Mechanism of Action of OmCI

Figure 8:
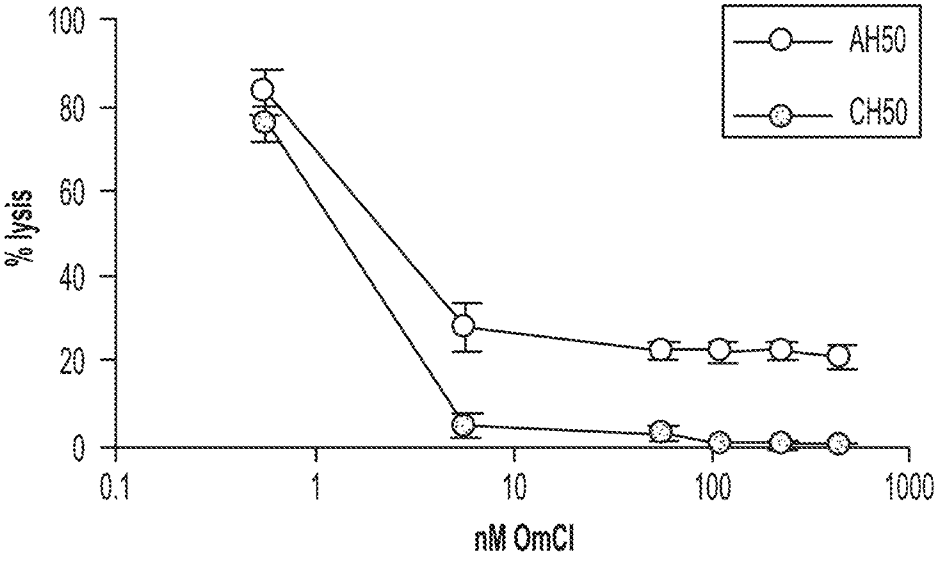
FIG. 8: Inhibition of lysis caused by classical (CH50) and alternative (AH50) pathways of complement activation by different concentrations of native OmCI. Average of 4 replicates.

OmCI inhibits both complement pathways. However while the classical pathway can be entirely inhibited, even excess OmCI inhibits lysis of red blood cells by the alternative pathway by no more than 80% (FIG. 8).

Figure 9:
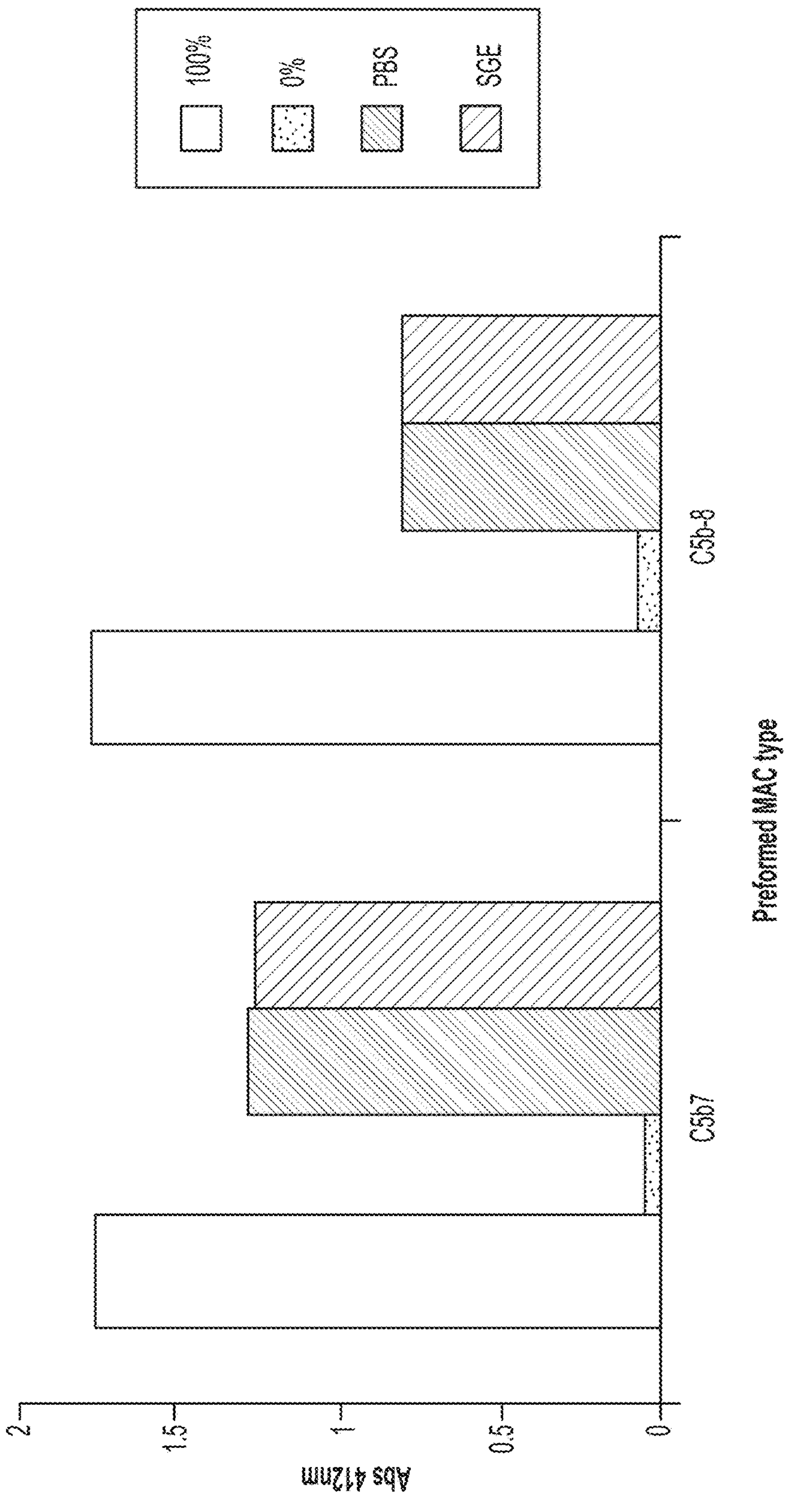
FIG. 9: Effect of OmCI on addition of C8 and C9 to partially formed membrane attack complex (MAC). Absorbance due to 100% and 0% lysis and in absence (PBS) and presence (SGE) of inhibitor shown. Average of 6 replicates.
Figure 10A:
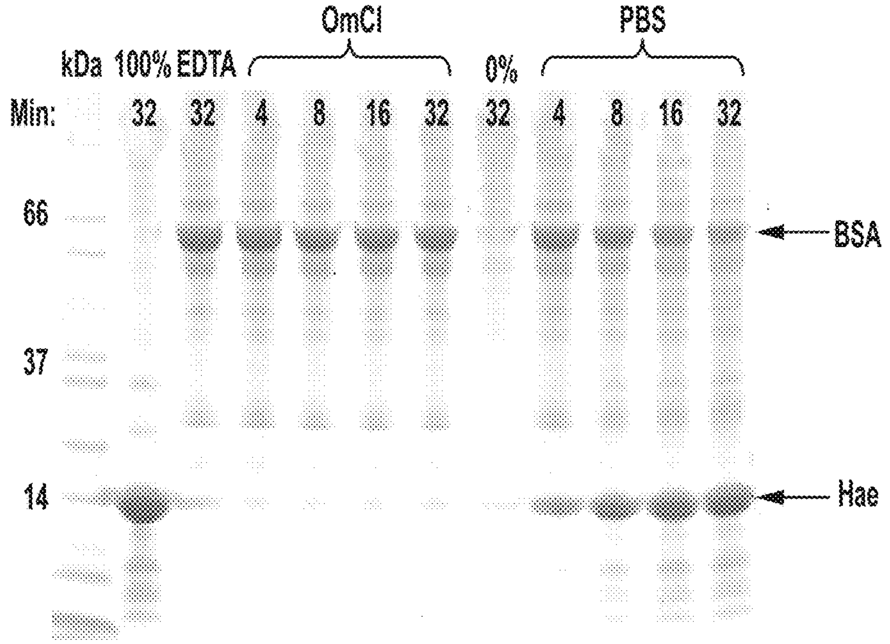
FIG. 10A: Timecourse showing absence of effect of OmCI on classical pathway cleavage of C3a from C3α analysed by denaturing SDS-PAGE. Minutes (min) since start of reaction indicated. Reactions performed with (OmCI) or without (PBS) inhibitor, or in presence of 10 mM EDTA. Positions of bovine serum albumin (BSA) and haemoglobin (HAE) shown. Size markers (kDa) indicated at left of panel.
Figure 10B:
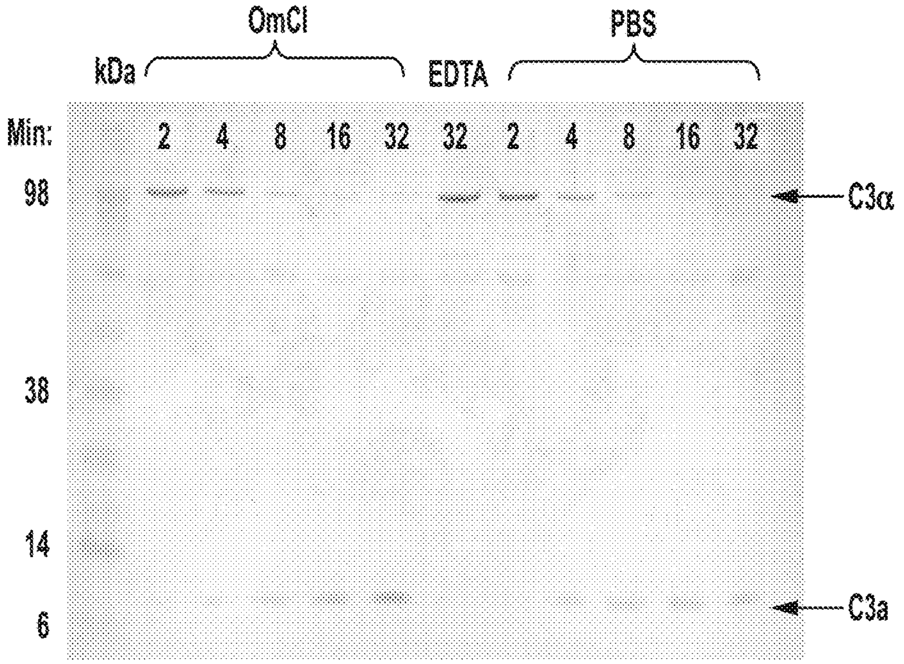
FIG. 10B: Timecourse showing absence of effect of OmCI on classical pathway cleavage of C3a from C3α analysed by immunoblot with C3a specific antisera. As FIG. 10A, positions of C3a and C3α shown.
Figure 11:
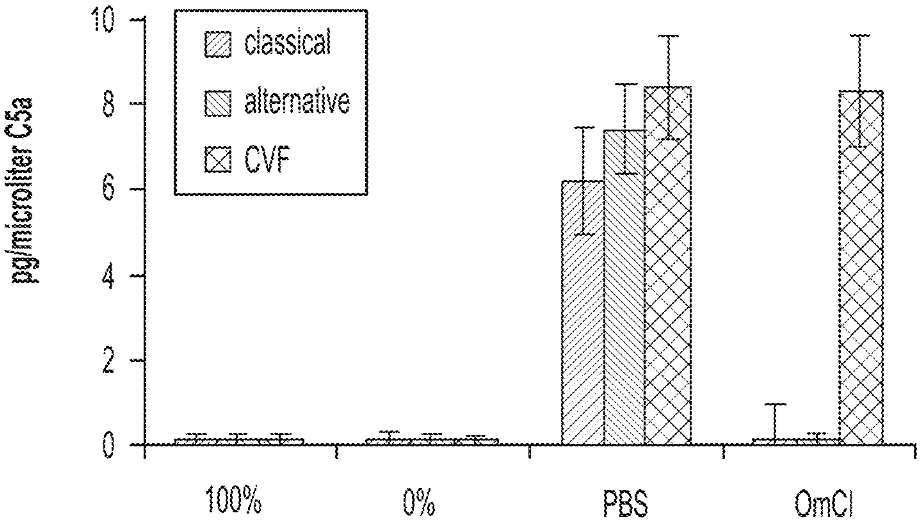
FIG. 11: Effect of OmCI on classical, alternative and cobra venom factor (CVF) C5 convertase cleavage of C5a from C5α analysed by ELISA. Picograms/μl C5a released measured after 100% lysis of sheep red blood cells with water, 0% lysis in $GVB^2$ only, and reactions with (OmCI) or without (PBS) inhibitor. Average of 4 replicates.
Figure 12:
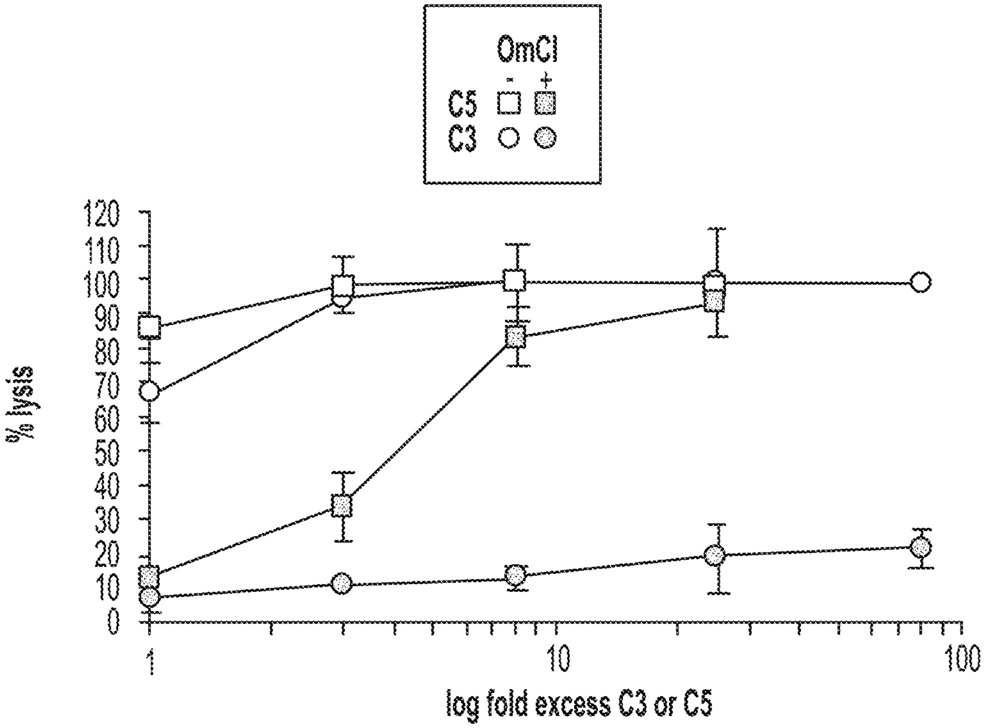
FIG. 12: Effect of addition of pure C3 and C5 to C3 and C5 depleted sera on classical pathway lysis of sheep red blood cells in presence (+) and absence (−) of minimal amount of OmCI that gave complete inhibition of lysis at 1 log fold excess. Average of 4 replicates.

OmCI does not prevent incorporation of C8 and C9 into preformed C5b-7 or C5b-8, respectively (FIG. 9). Nor does it affect the rate of C3α cleavage to yield C3a by either the classical or the alternative pathways (FIG. 10). OmCI does prevent production of C5a from C5 by both pathways (FIG. 11). Excess pure C5, but not C3 out-competes, the OmCI inhibitor in the classical haemolytic assay (FIG. 12). OmCI does not prevent decomplementation of sera by CVF (data not shown). Nor does it prevent C5a production by the CVF C3/C5 convertase (CVFBb) (FIG. 11).

Thermostability and pH Stability of Native OmCI

Figure 13:
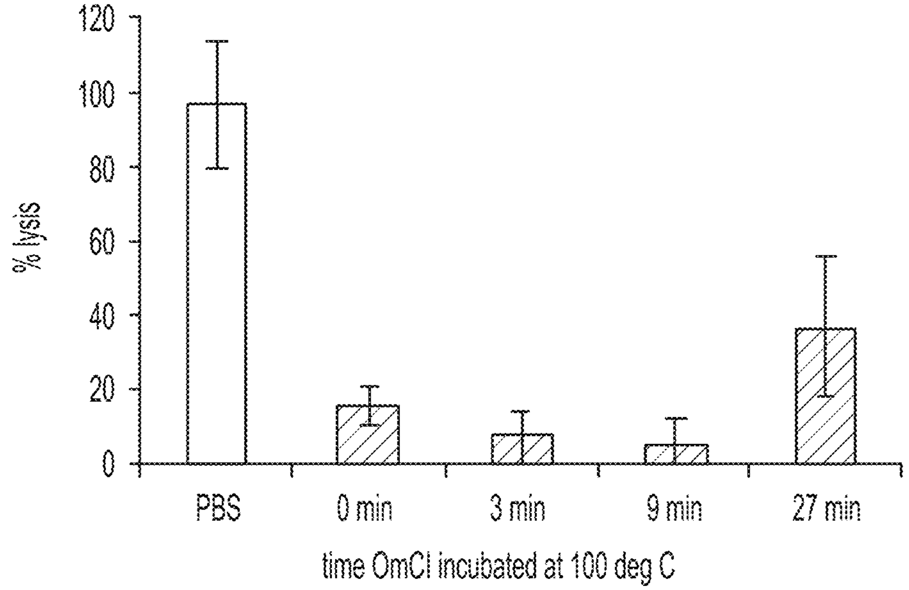
FIG. 13: Effect of boiling on inhibitory activity of OmCI in CH50 assay.
Figure 14:
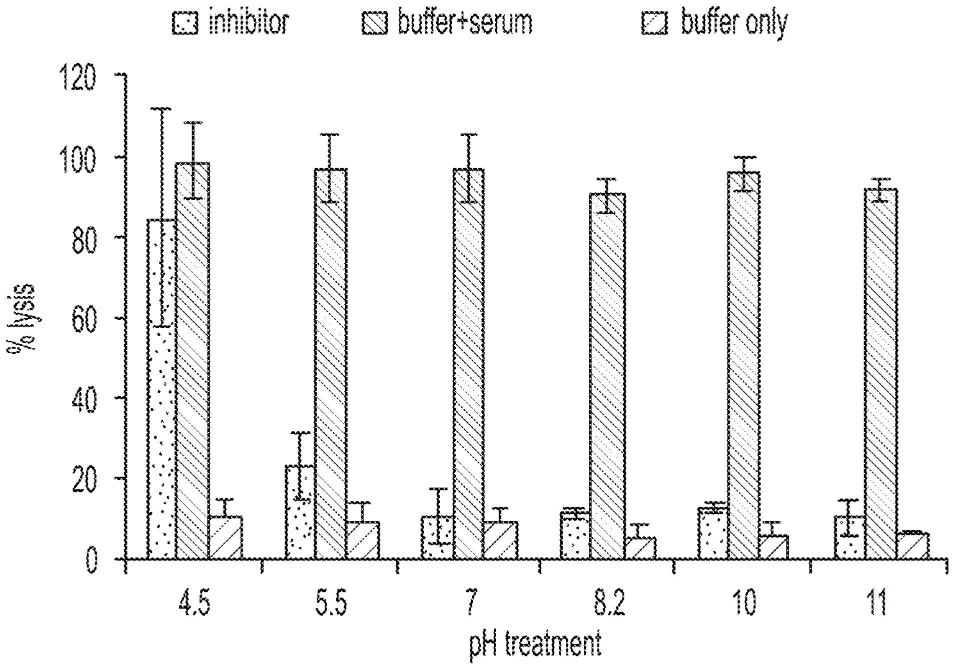
FIG. 14: Effect of pH treatment on inhibitory activity of OmCI in CH50 assay.

Boiling OmCI for up to 9 minutes did not have a significant affect on the inhibitory activity of the protein, although by 27 minutes inhibitory activity had decreased (FIG. 13). Native OmCI was unaffected by exposure to alkaline buffers up to pH 11 (FIG. 14). Exposure to buffer of pH 4.5 markedly decreased the inhibitory activity of OmCI (FIG. 14). Silver stained gels showed that this was not simply due to precipitation of OmCI at this pH (data not shown).

Detection of C5 Binding to OmCI

Figure 15:
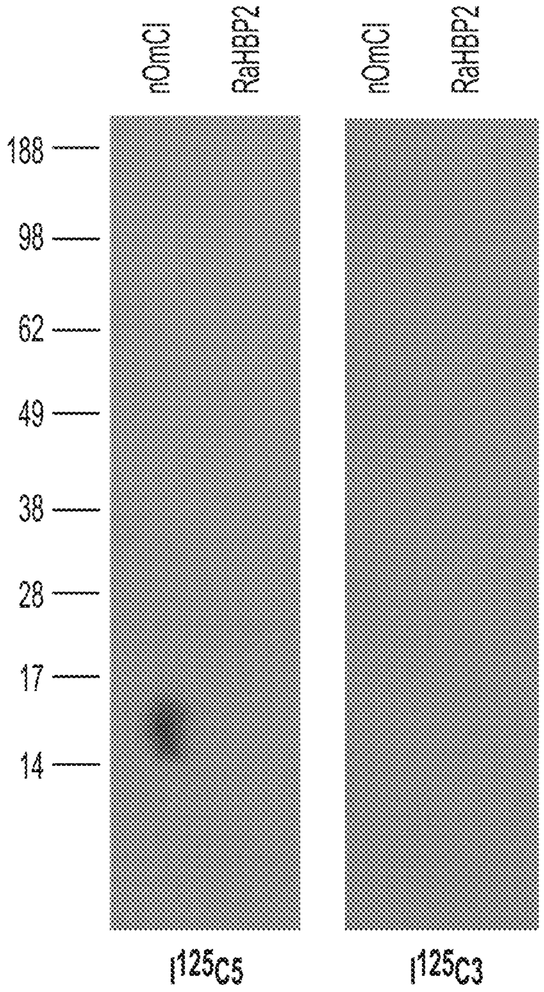
FIG. 15: Detection of C5 binding to nOmCI. nOmCI and RaHBP2 (control) transferred to nitrocellulose were probed with $I^{125}$ labelled C3 or C5 then autoradiogramed. Protein size markers (kDa) indicated at left of panel.

Western blotting with $I^{125}$ labelled C3 and C5 indicates that OmCI binds directly to C5 but not to the related protein C3 (FIG. 15).

Figure 16A:
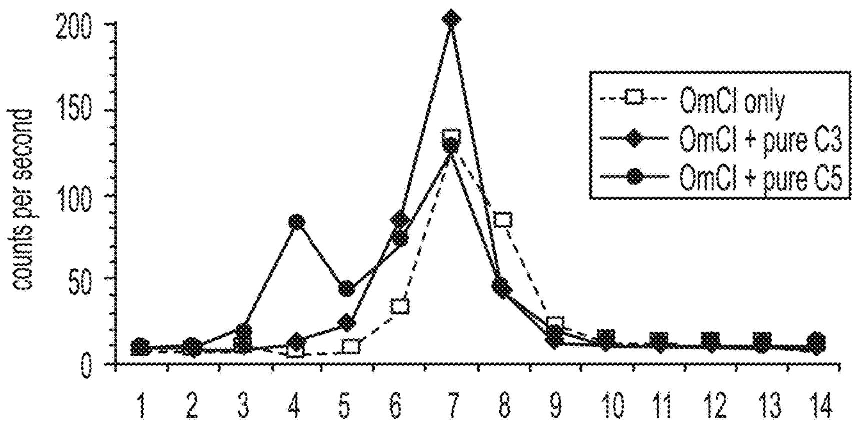
FIG. 16A: Detection of nOmCI binding to C5 by gel filtration chromatography. Radiolabelled nOmCI with or without purified C3 and C5 (pure C3/C5).
Figure 16B:
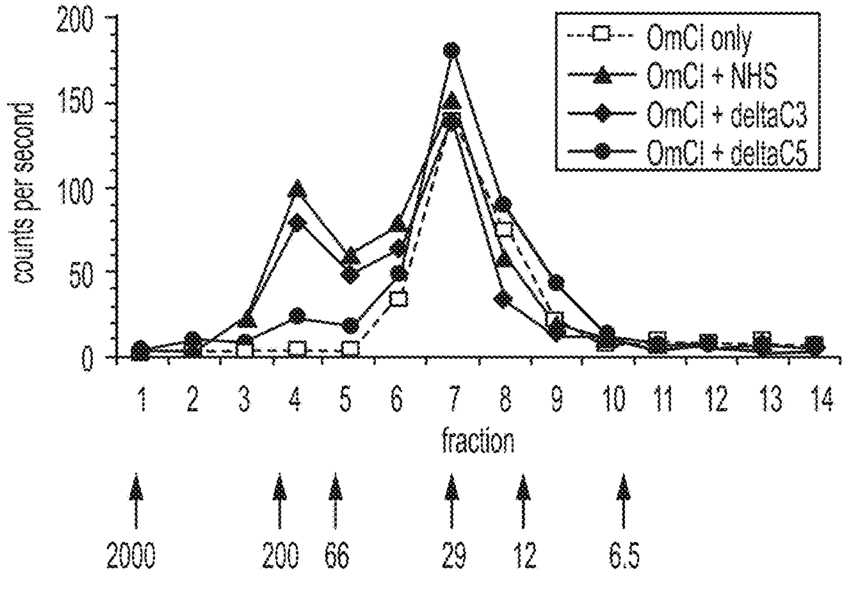
FIG. 16B: Detection of nOmCI binding to C5 by gel filtration chromatography. Radiolabelled nOmCI with or without NHS, and C3 or C5 depleted sera (delta C3/C5). Protein size markers (kDa) indicated by arrows.

Additional evidence for a direct interaction between OmCI and C5 was obtained by gel filtration chromatography. An apparent mass shift in a proportion of the $I^{125}$ labelled nOmCI was observed in the presence of purified C5 but not C3 (FIG. 16*a*). A similar mass shift was evident in the presence of NHS and C3 depleted sera but not C5 depleted sera (FIG. 16*b*). The mass shift was maintained in the presence of 1M NaCl but not 2M NaCl indicating a strong electrostatic interaction between the inhibitor and C5 (data not shown).

Discussion

Relationship to Other Proteins and to Known Complement Inhibitors

OmCI is most closely related to tick salivary gland proteins 2 and 3 (TSGP2 and 3) of the soft tick *O. savignyi* (Mans et al., 2001) and the platelet aggregation inhibitor moubatin (Waxman and Connolly, 1993). It has not been shown, or suggested, that any of these three proteins (FIG. 5) inhibit complement. The two small amino acid insertions present in OmCI but not in the closely related proteins (FIG. 5) are obvious sites to focus on in future mutagenesis studies to define complement binding sites in OmCI.

TSGP2 and 3 have 95% amino acid identity and have been proposed to have roles in the granule biogenesis of tick salivary glands (Mans et al, 2001). TSGP2 is toxic to mice; TSGP3 is not (Mans et al, 2002). OmCI is highly unlikely to be a toxin since *O. moubata* is non-toxic (Astigarraga et al., 1997) whereas *O. savignyi* causes sand tampan toxicoses in a wide range of mammals (Mans et al, 2002). Furthermore, inoculation of guinea pigs with 100 μg of purified native OmCI, in the process of raising antisera, caused no obvious pathophysiological effects (personal observation).

OmCI is probably a member of the lipocalin family of proteins that include the histamine binding protein family of tick specific proteins (Paesen et al., 2000). Lipocalins predominantly bind small, hydrophobic, extracellular ligands within their beta-barrel structures. However, the histamine binding protein of the tick *Rhipicephalus appendiculatus* has significant structural differences from normal lipocalins that enable it to bind hydrophilic molecules (Paesen et al., 1999; Paesen et al., 2000). It is not yet known whether OmCI binds any small ligands.

The primary sequence of OmCI has no detectable similarity to complement control protein (CCP) domains (multiple c.60 amino acid repeats) which form many of the bodies own complement inhibitors including factor H, C4BP, CR1, CR2, MCP and DAF). Nor is it similar to any other known complement inhibitors in public databases including Isac, the salivary complement alternative pathway inhibitor protein of *Ixodes scapularis* (Valenzuela et al., 2000). It is also unrelated to the N-terminal sequence of *O. moubata* antigen 20A1 (Baranda et al., 2000) which was proposed to be the factor responsible for the potent complement inhibition previously observed in the SGE's of *O. moubata* and *O. erraticus* (Astigarraga et al., 1997).

Mechanism of Complement Inhibition

Both glycosylated and deglycosylated rOmCI expressed in yeast are as potent as the native protein purified from SGE. C-terminal histidine tagged OmCI expressed in insect cells is not as potent (data not shown). OmCI inhibits both the classical and alternative pathways of complement activation of both humans and guinea pigs and presumably other mammals as well. This property should prove useful in defining precisely how OmCI works, and will be invaluable in the development of animal models of complement mediated diseases where the species specificity of present C5 inhibitors have hampered in vivo studies using rodents (Link et al., 1999).

OmCI does not inhibit either the classical (C4bC2a) or the alternative (C3bBb) C3 convertase since it has no effect on the rate of C3α cleavage (FIG. 10). OmCI does prevent production of C5a from C5 (FIG. 11). Since excess C5 out-competes the OmCI inhibitor (FIG. 12) functional classical (C4bC2aC3b) and alternative ($C3b^2Bb$) C5 convertases must be formed in the presence of the tick inhibitor. OmCI is unlikey to be a direct serine protease inhibitor of the convertase catalytic components C2a and Bb or it would prevent C3a as well as C5a production. The inhibitor does not prevent C5a production by the CVF C3/C5 convertase (CVFBb) (FIG. 11) which suggests OmCI does not bind C5 and block the C5a cleavage site. The latter finding does not exclude the possibility that OmCI binds to a site on C5 that prevents binding to the normal serum C5 convertases but not to the CVF convertase (Sandoval et al., 2000).

Two independent lines of evidence suggest OmCI activity is mediated through direct binding to C5 (FIG. 15 and FIG. 16).

Although OmCI inhibits both complement pathways, even with excess inhibitor the alternative pathway is inhibited by at most 80% (FIG. 8). This is explicable in terms of the different C5 convertases used by the classical (C4bC2aC3b) and alternative ($C3b^2Bb$) pathways, but the mechanism remains to be explored.

In summary, OmCI probably either binds C5 and prevents it interacting with the C5 convertases or binds the C5 convertases and C5 and prevents C5 cleavage. Presently we have no compelling evidence supporting one possibility over the other.

Thermostability and pH Stability of Native OmCI

OmCI is thermostable but activity begins to be lost after being boiled for 27 minutes. OmCI appears to be sensitive to acid and insensitive to alkali. Both prolonged boiling and exposure to acid probably induce conformational changes that inactivate the protein.

REFERENCES

Altschul, S. F., Madden, T. L., Schaffer, A. A., Zhang, J., Zhang, Z., Miller, W., and Lipman D. J. (1997). Gapped BLAST and PSI-BLAST a new generation of protein database search programs. *Nucleic Acids Res.,* 25, 3389-3402.

Astigarraga, A., Oleaga-Perez, A., Perez-Sanchez, R., Baranda, J. A., Encinas-Grandes, A. (1997). Host immune response evasion stratagies in *Ornothodoros erraticus* and *O. moubata* and their relationship to the development of an antiargasid vaccine. *Parasite Immunol.* 19, 401-410.

Bao. L., Haas, M., Boackle, S. A., Kraus, D. M., Cunningham, P. N., Park, P., Alexander, J. J., Anderson, R. K., Culhane, K., Holers, V. M., and Quigg, R. J. (2002). Transgenic expression of a soluble complement inhibitor protects against renal disease and promotes survival in MRL/pr mice. *J. Immunol.* 168, 3601-7.

Baranda, J. A., Perez-Sanchez, R., Oleaga, A., Manzano, R., Encinas-Grandes, A. (2000). Purification N-terminal sequencing and diagnostic value of the major antigens of *Ornithodoros erraticus* and *O. moubata*. Veterinary Parasit. 87, 193-206.

Bateman, A., Birney, E., Durbin, R., Eddt, S. R., Howe, K. L., and Sonnhammer, E. L. (2000). The Pfam protein families database. *Nucleic Acids Res.* 28, 263-266.

Bedford, J. M., and Witkin S. M. (1983). Influence of complement depletion on sperm function in the female rabbit. *J. Reprod. Fertil.* 69, 523-528.

Biesecker, G., Dihel, L., Enney, K., Bendele, R. A. (1999). Derivation of RNA aptamer inhibitors of human complement C5. *Immunopharmacology* 42, 219-30.

Ciccheti, F., Costantini, L., Belizaire, R., Burton, W., Isacson, O., and Fodor, W. (2002). Combined inhibition of apoptosis and complement improves neural graft survival of embryonic rat and porcine mesencephalon in the rat brain. Exp. Neurol. 177, 376-84.

Coligan, J. E. (1994). Complement. In "Current Protocols in Immunology". (J. E. Coligan, A. M. Kruisbeek, D. H. Marguiles, E. M. Shevach, and W. Strober, Eds.). Wiley Interscience.

Daha, M. R. (1993). In *Complement in health and disease,* 2nd edition, (ed. K. Whaley), p 185. MTP, Lancaster.

Diamond, L. E., McCurry, K. R., Oldham, E. R., Tone, M., Waldmann, H., Platt, J. L., and Logan, J. S. (1995). Human CD59 expressed in transgenic mouse hearts inhibits the activation of complement. *Transpl. Immunol.* 3, 305-312.

Dodds, A. W., and Sim, R. B. (1997). *Complement*, The Practical Approach Series (series eds. D. Rickwood and B. D. Hames). Oxford University Press Inc., New York.

Ember, J. A., Jagels, M. A., Hugli, T. E. (1998). Characterisation of complement anaphylatoxins and and their biological responses. In: Volanakis, J. E., Frank, M. M. (Eds.), The Human Complement System in Health and Disease. Marcel Dekker, New York, pp 241-284.

Fecke, W., Long, J., Richards, A., Harrison, R. (2002). Protection of hDAF-transgenic porcine endothelial cells against activation by human complement: role of the membrane attack complex. *Xenotransplantation* 9, 97-105.

Fernandez & Hoeffler (1998) Gene Expression Systems: Using Nature for the Art of Expression, Academic Press, San Diego, London, Boston, New York, Sydney, Tokyo, Toronto.

Fiorante, P., Banz, Y., Mohacsi, P. J., Kappeler, A., Wuillemin, W. A., Macchiarini, P., Roos, A., Daha, M. R., Schaffner, T., Haeberli, A., Mazmanian, G. M., and Rieben, R. (2001). Low molecular weight dextran sulfate prevents complement activation and delays hyperacute rejection in pig-to-human xenotransplantation models. *Xenotransplantation* 8, 24-35.

Fitch, J. C., Rollins, S., Matis, L., Alford, B., Aranki, S., Collard, C. D., Dewar, M., Elefteriades, J., Hines, R., Kopf, G., Kraker, P., Li, L., O'Hara, R., Rinder, C., Shaw, R., Smith, B., Stahl, G., and Shernan, S. K. (1999). Pharmacology and biological efficacy of a recombinant, humanised, single-chain antibody C5 complement inhibitor in patients undergoing coronary artery bypass graft surgery with cardiopulmonary bypass. *Circulation,* 100, 2499-506.

Frei, Y., Lambris, J. D., and Stockinger, B. (1987). Generation of a monoclonal antibody to mouse C5 application in an ELISA assay for detection of anti-C5 antibodies. *Mol. Cell. Probes* 1, 141-149.

Giclas, P. C. (1994). Classical and alternative pathway evaluation (sections 13.1 and 13.2). In *Current Protocols in Immunology, Vol.* 3, *Complement*. Editors: J. E. Coligan, A. M. Kruisbeek, D. H. Marguiles, E. M. Shevach and W. Strober. Series editor: R. Coico. John Wiley and Sons, Inc., USA.

Homeister, J. W., Satoh, P., and Lucchesi, B. R. (1992). Effects of complement activation in the isolated heart. Role of the terminal complement components. *Circ. Res.* 71, 303-319.

Hebell, T., Ahearn, J. M., and Fearon, D. T. (1991). Suppression of the immune response by a soluble complement receptor of B lymphocytes. *Science,* 254, 102-105.

Jarvis, J. N., Lockman, J. C., and Levine, R. P. (1993). IgM rheumatoid factor and the inhibition of covalent binding of C4b to IgG in immune complexes. *Clin. Exp. Rheumatol.* 11, 135-141.

Jeanmougin, F., Thompson, J. D., Gouy, M., Higgins, D. G., and Gibson, T. J. (1998). Multiple sequence alignment with Clustal X. *Trends Biochem. Sci.* 23, 403-405.

Jones, L. D., Davies, C. R., Steele, G. M. and Nuttall, P. A. (1988). The rearing and maintenance of ixodid and argasid ticks in the laboratory. *Animal Technology* 39, 99-106.

Kohl, J. (2001). Anaphylatoxins and infectious and non-infectious inflammatory diseases. *Molecular Immunology* 38, 175-187.

Kontinnen, Y. T., Ceponis, A., Meri, S., Vuorikoski, A., Kortekangas, P., Sorsa, T., Sukura, A., and Santavirta S. (1996). Complement in acute and chronic arthritides:

assessment of C3c, C9, and protectin (CD59) in synovial membrane. *Ann. Rheum. Dis.* 55, 888-894.

Kroshus, T. J., Salerno, C. T., Yeh, C. G., Higgins, P. J., Bolman, R. M., and Dalmasso, A. P. (2000). A recombinant soluble chimeric complement inhibitor composed of human CD46 and CD55 reduces acute cardiac tissue injury in models of pig-to-human heart transplantation. *Transplantation,* 69, 2282-9.

Law, S. K. A., and Reid K. B. M. (1995). *Complement*, Second edition, (ed. D. Male). Oxford University Press, Oxford.

Link, C., Hawlisch, H., Meyer zu Vilsendorf, A., Gyleruz, S., Nagel, E., and Kohl, J. (1999). Selection of phage-displayed anti-guinea pig C5 or C5a antibodies and their application in xenotransplantation. *Mol. Immunol.* 36, 1235-47.

Mans, B. J., Venter, J. D., Very, P. J., Louw, A. I., Neitz, A. W. (2001). Identification of putative proteins involved in granule biogenesis of tick salivary glands. *Electrophoresis,* 22, 1739-1746.

Mans, B. J., Steinmann, C. M. L., Venter J. D., Louw A. I., and Neitz, A. W. H. (2002). Pathogenic mechanisms of sand tampan toxicoses induced by the tick, *Ornithodoros savignyi. Toxicon* 40, 1007-1016.

Miletic, V. D., and Popovic O. (1993). Complement activation in stored platelet concentrates. *Transfusion* 33, 150-154.

Mulligan, M. S., Warner, R. L., Rittershaus, C. W., Thomas, L. J., Ryan, U. S., Foreman, K. E., Crouch, L. D., Till, G. O., and Ward, P. A. (1999). Endothelial targeting and enhanced antiinflammatory effects of complement inhibitors possessing sialyl Lewisx moieties. *J. Immunol.* 162, 4952-9.

Paesen, G. C., Adams, P. L., Harlos, K., Nuttall, P. A., and Stuart, D. I. (1999). Tick histamine binding proteins: isolation, cloning, and three-dimensional structure. *Molecular Cell* 3, 661-671.

Paesen, G. C., Adams, P. L., Nuttall, P. A., and Stuart, D. L. (2000). Tick histamine-binding proteins: lipocalins with a second binding cavity. *Biochim. Biophys. Acta.* 1482, 92-101.

Pratt, J. R., Hibbs, M. J., Laver, A. J., Smith, R. A., and Sacks S. H. (1996). Effects of complement inhibition with soluble complement receptor-1 on vascular injury and inflammation during renal allograft rejection in the rat. *Am. J. Pathol.* 149, 2055-2066.

Rehrig, S., Fleming, S. D., Anderson, J., Guthridge, J. M., Rakstang, J., McQueen, C. E., Holers, V. M., Tsokos, G. C., Shea-Donohue, T. (2001). Complement inhibitor, complement receptor 1-related gene/protein y-Ig attenuates intestinal damage after the onset of mesenteric ischaemia/reperfusion injury in mice. *J. Immunol.* 167, 5921-7.

Ribeiro, J. M. C. (1987). *Ixodes dammini*: salivary anti-complement activity. *Exp. Parasitol.* 64, 347-353

Rollins, S. A., Birks, C. W., Setter, E., Squinto, S. P., and Rother, R. P. (1996). Retroviral vector producer cell killing in human serum is mediated by natural antibody and complement: strategies for evading the humoral immune response. *Hum. Gene Ther.* 7, 619-626.

Rollins, S. A., Fitch, J. C. K., Shernan, S., Rinder, C. S., Rinder, H. M., Smith, B. R., Collard, C. D., Stahl, G. L., Alford, B. L., Li, L., and Matis, L. A. (1998). Anti-C5 single chain antibody therapy blocks complement and leukocyte activation and reduces myocardial tissue damage in CPB patients. *Mol. Immunol.* 35, (1998), 397-397.

Sahu, A., and Lambris, J. D. (2000). Complement inhibitors: a resurgent concept in antiinflammatory therapeutics. *Immunopharmacology* 49, 133-148.

Sambrook, J. et al, (2000) Molecular Cloning, A Laboratory Manual, Cold Spring Harbor Laboratory Press, Cold Spring Harbor, N.Y.

Sandoval, A., Rong, A, Ostresh, J. M., and Ogata, R. T. (2000). Distal recognition site for classical pathway convertase located in the C345C/Netrin module of complement component C5. *The Journal of Immunology,* 165, 1066-73

Schiller, B., Cunningham, P. N., Alexander, J. J., Bao, L., Holers, V. M., and Quigg, R. J. (2001). Expression of a soluble complement inhibitor protetcs transgenic mice from antibody induced acute renal failure. *J. Am. Soc. Nephrol.* 12, 71-9.

Schultz, J., Copley, R. R., Doerks, T., Ponting, C. P., and Bork, P. (2000). SMART: a web based tool for the study of genetically mobile domains. *Nucleic Acids Res.* 28, 231-234.

Smith G. P., and Smith, R. A. G. (2001). Membrane-targetted complement inhibitors. *Mol. Immunol.* 38, 249-255.

Solomon, S., Kolb, C., Mohanty, S., Jeisy-Walder, E., Preyer, R., Schollhorn, V., and Illges, H. (2002). Transmission of antibody-induced arthritis is independent of complement component 4 (C4) and the complement receptors 1 and 2 (CD21/35). *Eur. J. Immunol.* 32, 644-51.

Tanaka, M., Murase, N., Ye, Q., Miyazaki, W., Nomoto, M., Miyazawa, H., Manez, R., Toyama, Y., Demetris, A. J., Todo, S., and Starzl, T. E. (1996). Effect of anticomplement agent K76 COOH on hamster-to-rat and guinea pig-to-rat xenotransplantation. *Transplantation* 62, 681-688.

Thomas, H., Maillet, F., Letourner, D., Jozefonvicz, J., Fischer, E., and Kazatchkine, M. D. (1996). Sulfonated dextran inhibits complement activation and complement dependent cytotoxicity in an in vitro model of hyperacute xenograft rejection. *Mol. Immunol.* 33, 643-648.

Vakeva, A. P., Agah, A., Rollins, S. A., Matis, L. A., Li, L., and Stahl, G. L. (1998). Myocardial infarction and apoptosis after myocardial ischemia and reperfusion—Role of the terminal complement components and inhibition by anti-C5 therapy. Circulation 97, 2259-2267.

Valenzuela, J. G., Charlab, R., Mather, T. N., Ribeiro, J. M. (2000). Purification, cloning, and expression of a novel salivary anticomplement protein from the tick, *Ixodes scapularis. J. Biol. Chem.,* 275, 18717-18723.

Wang, Y., Rollins, S. A., Madri, J. A., and Matis, L. A. (1995). Anti-C5 monoclonal antibody therapy prevents collagen-induced arthritis and ameliorates established disease. *Proc. Natl. Acad. Sci. U.S.A* 92, 8955-8959.

Wang, Y., Hu, Q. L., Madri, J. A., Rollins, S. A., Chodera, A., and Matis, L. A. (1996). Amelioration of lupus-like autoimmune disease in NZB/WF1 mice after treatment with a blocking monoclonal antibody specific for complement component C5. *Proc. Natl. Acad. Sci U.S.A* 93, 8563-8568.

Ward, P. A., Czermak, B. J., Huber-Lang, M., Diehl, K., and Friedl, H. P. (2000). Use of animal models to define complement functions. In: Lambris, J. D., Holers, V. M. (Eds.), Therapeutic Interventions in the Complement System. Humana Press, Totowa.

Weisman, H. F., Bartow, T., Leppo, M. K., Marsh, H. C. J, Carson, G. R., Concino, M. F., Boyle, M. P., Roux, K. H., Weisfeldt, M. L., and Fearon, D. T. (1990). Soluble human complement receptor type I: in vivo inhibitor of complement suppression post-ischaemic myocardial inflammmation and necrosis. *Science,* 249, 146-151.

Whaley, K., editor (1993). *Complement in health and disease,* 2nd edition. MTP, Lancaster.

Wyss-Coray, T., Yan, F., Lin, A. H., Lambris, J. D., Alexander, J. J., Quigg, R. J., and Masliah, E. (2002). Prominent neurodegeneration and increased plaque formation in complement-inhibited Alzheimer's mice. *Proc. Natl. Acad. Sci. U.S.A* 99, 10837-42.

Zhang, H., Lu, S., Morrison, S. L., and Tomlinson, S. (2001). Targetting of functional antibody decay accelerating factor fusion proteins to a cell surface. *J. Biol. Chem.* 276, 27290-5.

The invention claimed is:

1. A method of inhibiting cleavage of C5 in a mammal comprising:

administering to the mammal an isolated complement inhibitor, the inhibitor comprising i) an amino acid sequence with at least 90% sequence identity to amino acids 19 to 168 of SEQ ID NO: 2, or ii) an amino acid sequence with at least 90% sequence identity to amino acids 1 to 168 of SEQ ID NO: 2.

2. The method of claim 1, wherein the mammal is human.

3. The method of claim 1, wherein the mammal is suffering from a complement-mediated disease or disorder.

4. The method of claim 3, wherein the complement-mediated disease or disorder is an autoimmune disease, postoperative tissue damage, or transplant rejection.

5. The method of claim 4, wherein the complement-mediated disease or disorder is an autoimmune disease.

6. The method of claim 5, wherein the autoimmune disease is rheumatoid arthritis or glomerulonephritis.

7. The method of claim 4, wherein the complement-mediated disease or disorder is postoperative tissue damage.

8. The method of claim 7, wherein the postoperative tissue damage is reperfusion injury.

9. The method of claim 4, wherein the complement-mediated disease or disorder is transplant rejection.

10. The method of claim 3, wherein the complement-mediated disease or disorder is Alzheimer's disease.

11. The method of claim 3, wherein the complement-mediated disease or disorder is delayed-type hypersensitivity disorder, sepsis, or immune complex disorder.

12. The method of claim 1, wherein the method comprises administering a pharmaceutical composition comprising the isolated complement inhibitor and at least one pharmaceutically acceptable carrier to the mammal.

13. The method of claim 1, wherein the isolated complement inhibitor is administered in an amount ranging from 0.01 mg per kg mass of the mammal to 50 mg per kg mass of the mammal.

14. The method of claim 1, wherein the isolated complement inhibitor is administered in an amount ranging from 0.05 mg per kg mass of the mammal to 10 mg per kg mass of the mammal.

15. The method of claim 1, wherein the isolated complement inhibitor is administered in combination with at least one other agent.

16. The method of claim 15, wherein the at least one other agent is a drug or hormone.

17. The method of claim 12, wherein the isolated complement inhibitor has an amino acid sequence with at least 95% sequence identity to amino acids 19 to 168 of SEQ ID NO: 2.

18. The method of claim 1, wherein the isolated complement inhibitor was expressed from a plasmid vector.

19. The method of claim 1, wherein the isolated complement inhibitor was expressed from a viral vector.

20. The method of claim 1, wherein the isolated complement inhibitor was expressed in prokaryotic cells.

21. The method of claim 1, wherein the isolated complement inhibitor was expressed in transfected eukaryotic cells.

22. The method of claim 1, wherein the isolated complement inhibitor was expressed in cultured yeast, insect, or mammalian cells.

23. The method of claim 12, wherein the pharmaceutical composition comprises at least one pharmaceutically acceptable carrier selected from water, saline, glycerol, ethanol, a wetting agent, an emulsifying agent, and a pH buffering substance.

24. The method of claim 1, wherein the isolated complement inhibitor has an amino acid sequence with at least 95% sequence identity to amino acids 19 to 168 of SEQ ID NO: 2.

25. The method of claim 1, wherein the isolated complement inhibitor has an amino acid sequence with at least 98% sequence identity to amino acids 19 to 168 of SEQ ID NO: 2.

26. The method of claim 1, wherein the isolated complement inhibitor has an amino acid sequence of amino acids 19 to 168 of SEQ ID NO: 2.

27. The method of claim 1, wherein the isolated complement inhibitor inhibits at least one pathway of complement activation.

28. The method of claim 27, wherein the isolated complement inhibitor inhibits the classical pathway of complement activation.

29. The method of claim 27, wherein the isolated complement inhibitor inhibits the alternative pathway of complement activation.

30. The method of claim 27, wherein the isolated complement inhibitor inhibits the alternative pathway of complement activation and the classical pathway of complement activation.

31. A method of inhibiting cleavage of C5, comprising administering to a mammal an isolated complement inhibitor, the isolated complement inhibitor comprising a fragment of the complement inhibitor polypeptide of SEQ ID NO: 2, wherein said fragment comprises six cysteine residues that are spaced relative to each other at a distance of 32 amino acids apart, 62 amino acids apart, 28 amino acids apart, 1 amino acid apart, and 21 amino acids apart as arranged from the amino terminus to the carboxyl terminus of SEQ ID NO: 2.

32. The method of claim 31, wherein the method comprises administering a pharmaceutical composition comprising the isolated complement inhibitor and at least one pharmaceutically acceptable carrier to the mammal.

33. The method of claim 31, wherein the mammal has sepsis, immune complex disease or delayed-type hypersensitivity.

34. The method of claim 31, wherein the isolated complement inhibitor is administered in an amount ranging from 0.01 mg per kg mass of the mammal to 50 mg per kg mass of the mammal.

35. The method of claim 31, wherein the isolated complement inhibitor is administered in combination with at least one other agent.

36. The method of claim 31, wherein the mammal is a human.

37. The method of claim 31, wherein the isolated complement inhibitor was expressed from (i) a plasmid or viral vector and/or (ii) in prokaryotic or transfected eukaryotic cells.

38. The method of claim 31, wherein the pharmaceutical composition comprises at least one pharmaceutically acceptable carrier selected from water, saline, glycerol, ethanol, a wetting agent, an emulsifying agent, and a pH buffering substance.

39. The method of claim 31, wherein the method comprises administering a pharmaceutical composition comprising the isolated complement inhibitor and at least one pharmaceutically acceptable carrier to the mammal.

* * * * *